(12) United States Patent
Fujisawa et al.

(10) Patent No.: US 8,625,873 B2
(45) Date of Patent: Jan. 7, 2014

(54) MEDICAL IMAGE PROCESSING APPARATUS

(71) Applicants: Kabushiki Kaisha Toshiba, Tokyo (JP); Toshiba Medical Systems Corporation, Otawara (JP)

(72) Inventors: Yasuko Fujisawa, Nasushiobara (JP); Shinsuke Tsukagoshi, Nasushiobara (JP); Yoshihiro Ikeda, Sakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/774,229

(22) Filed: Feb. 22, 2013

(65) Prior Publication Data

US 2013/0223589 A1 Aug. 29, 2013

(30) Foreign Application Priority Data

Feb. 24, 2012 (JP) .................................. 2012-038600
Feb. 24, 2012 (JP) .................................. 2012-038660

(51) Int. Cl.
*G06K 9/00* (2006.01)

(52) U.S. Cl.
USPC . 382/131; 382/128; 250/363.02; 250/363.04; 250/363.05

(58) Field of Classification Search
USPC ........ 382/128, 131; 250/455, 363.02, 363.04, 250/363.05
See application file for complete search history.

(56) References Cited

U.S. PATENT DOCUMENTS

| 5,630,034 | A | * | 5/1997 | Oikawa et al. | ................ | 345/424 |
| 2003/0021385 | A1 | * | 1/2003 | Izuhara | ........................ | 378/195 |
| 2005/0275654 | A1 | * | 12/2005 | Matsumoto | ................... | 345/421 |
| 2010/0014760 | A1 | * | 1/2010 | Mohammad et al. | ......... | 382/203 |
| 2010/0098299 | A1 | * | 4/2010 | Muquit et al. | ................ | 382/115 |
| 2010/0202675 | A1 | | 8/2010 | Takanaka et al. | | |

FOREIGN PATENT DOCUMENTS

JP 2010-201157 9/2010
JP 2010-284301 12/2010

* cited by examiner

*Primary Examiner* — Ali Bayat
(74) *Attorney, Agent, or Firm* — Oblon, Spivak, McClelland, Maier & Neustadt, L.L.P.

(57) ABSTRACT

Provided is a medical image processing apparatus allowing the generation of image data by changing the reconstruction conditions in correspondence with the positional relation of an observation target based on the projected data chronologically acquired by an X-ray CT scanner. The medical image processing apparatus includes a photographing unit, a reconfiguration processing unit, an extracting unit, and an analyzing unit. The photographing unit scans the flexible site of the living body configured from multiple parts in order to acquire projected data. The reconfiguration processing unit carries out reconfiguration processing on the projected data and generates image data of the flexible site regarding the plurality of timing points. The extracting unit extracts the plurality of components configuring the flexible site from the respective image data. The analyzing unit obtains the positional relation of the plurality of components.

25 Claims, 15 Drawing Sheets

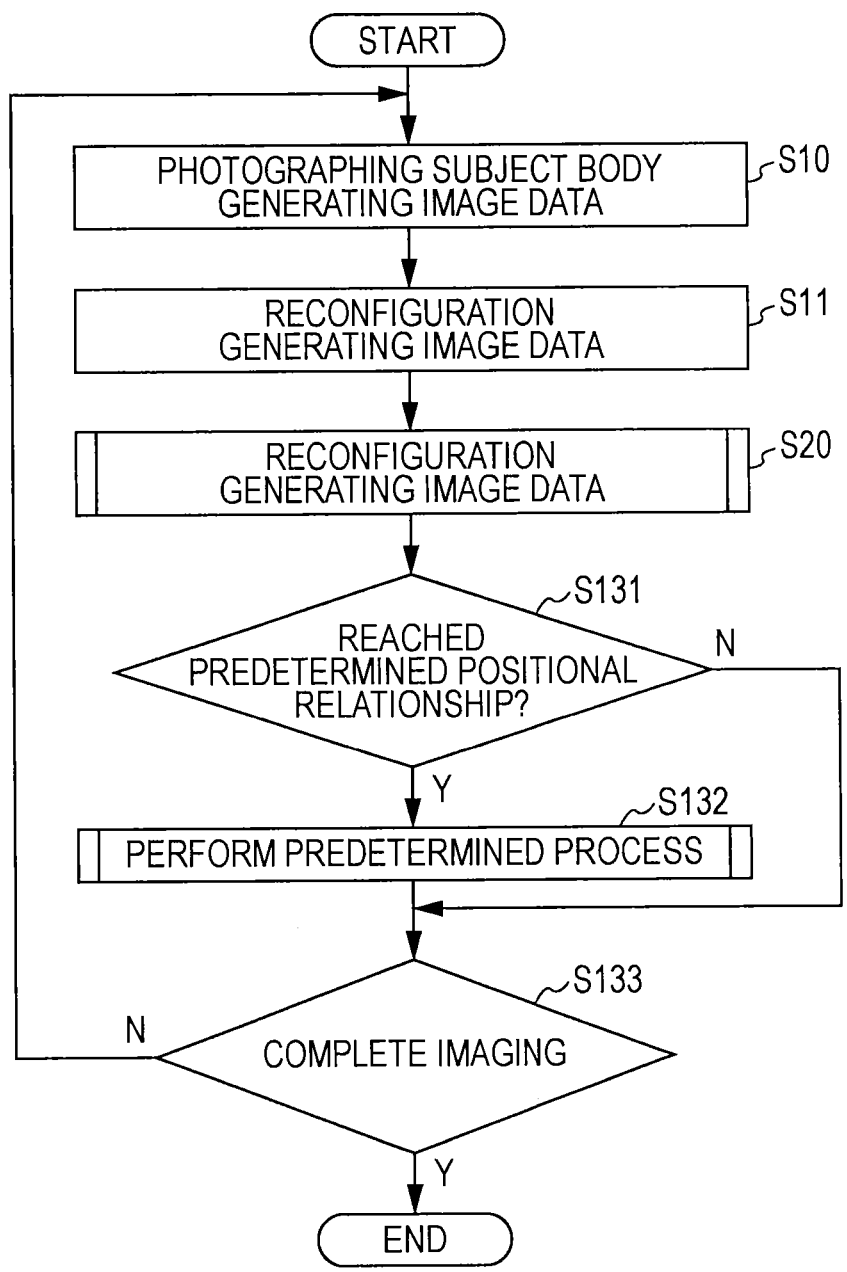

MEDICAL IMAGE PROCESSING APPARATUS

CROSS-REFERENCE TO RELATED APPLICATION

This application is based upon and claims the benefit of priority from Japanese Patent Applications No. 2012-038600 and No. 2012-038660, filed on Feb. 24, 2012; the entire contents of which are incorporated herein by reference.

FIELD

The embodiment relates to a technology for generating medical images based on a projection data obtained using an X-ray CT scanner.

BACKGROUND

An apparatus that uses an X-ray CT (Computed Tomography) scanner to scan test objects and processes the collected data with a computer, thereby imaging the inside of the test object.

Specifically, the X-ray CT scanner exposes X-rays onto the test object from different directions multiple times, extracts the X-rays penetrating the test object to an X-ray detector, and collectes multiple detection data. The collected detection data is A/D-converted in a data collection unit, then sent to a console apparatus. The console apparatus carries out pretreatment, etc. on the detected data and produces projected data. Then, the console apparatus carries out reconfiguration processing based on the projected data and produces volume data based on tomographic image data or a plurality of tomographic image data. The volume data is data set expressing a 3-dimensional distribution of a CT number corresponding to a 3-dimensional region of the test object.

Moreover, the X-ray CT system includes an apparatus such as a multi-slice X-ray CT system that can carry out high-definition (high resolution) imaging over a wide range per unit time. This multi-slice X-ray CT system uses detector elements in m column in an anteroposterior direction and the n rows in the direction orthogonally intersecting the anteroposterior direction as the detector used in the single slice X-ray CT system, that is, a two-dimensional detector of a configuration with the m columns and n rows arranged.

Due to such a multi-slice X-ray CT system, the larger a detector is (the greater the number of detector elements configuring the detector), the greater the possibility of acquiring projection data over a wider region in a single image. In other words, by imaging with a multi-slice X-ray CT system provided with such a detector over time, it is possible to generate volume data for a specific site at a high frame rate (hereinafter, sometimes referred to as a "Dynamic Volume scan"). This makes it possible for an operator to assess the movement of the specific region within a unit of time by means of three-dimensional images.

In addition, a medical image processing apparatus exists that reconstructs volume data and generates medical images from the volume data based on projected data obtained by the X-ray CT system.

BRIEF DESCRIPTION OF THE DRAWINGS

FIG. 5 is a flow chart showing a series of operations of the medical image processing apparatus according to the present embodiment.

DETAILED DESCRIPTION

The purpose of the embodiment is to provide a medical image processing apparatus capable of changing the reconstruction conditions according to the positional relation of the observation subject and generating the image data based on the projected data over time obtained by the X-ray CT system. Moreover, another purpose is to provide the X-ray CT system allowing to control the operation according to acquiring the projected data in correspondence with the positional relation of the observation subject during acquiring of the projected data.

The meaning of "in correspondence with the positional relation of the observation subject" includes a case of high degree of correspondence as a result of matching by means of external images obtained by imaging the observation subject, for example. It is intended to allow generation of image data by changing reconfiguration conditions and/or to allow controlling actions accompanied by obtaining projection data. These external images may be projection data, perspective data through computed tomography or angiography, or data obtained by videography.

The present embodiment pertains to a medical image processing apparatus comprising a photographing unit, a reconfiguration processing unit, an extracting unit, and an analyzing unit in order to achieve the purposes. The photographing unit scans flexible site of the living body configured from multiple parts and acquires the projected data. The reconfiguration processing unit carries out reconfiguration processing on the projected data and generates the image data of the flexible site regarding plurality of timing points. The extracting unit extracts a plurality of components configuring the flexible sites from the respective image data. The analyzing unit obtains the positional relation of the plurality of components configuring the extracted flexible site regarding a plurality of timing point and conditionally determines the obtained positional relation, thereby specifying the image data of the specific timing corresponding with the determination result.

Embodiment 1

Figure 1A:
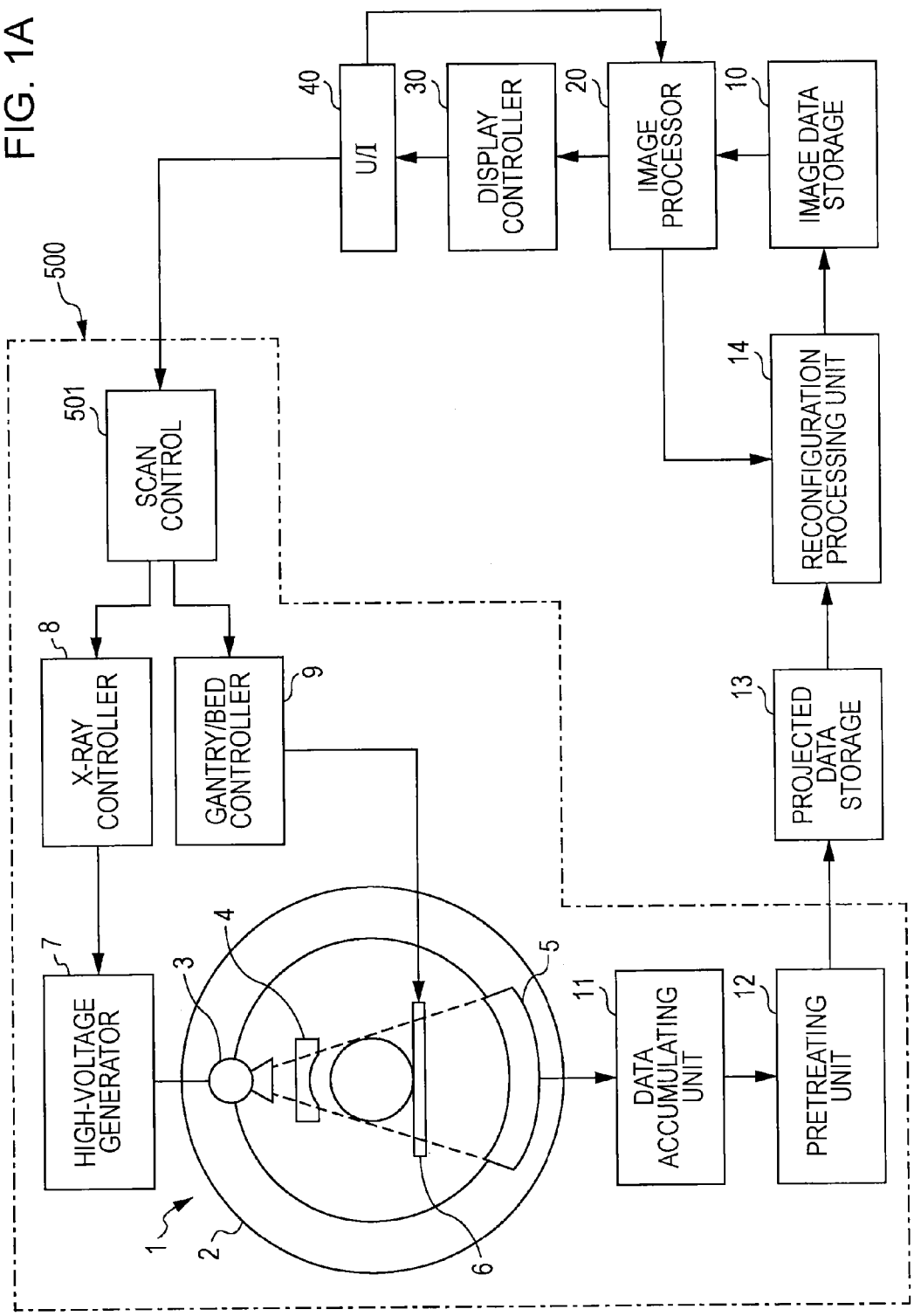
FIG. 1A is a block diagram showing the configuration of the medical image processing apparatus according to the present embodiment.
Figure 1B:
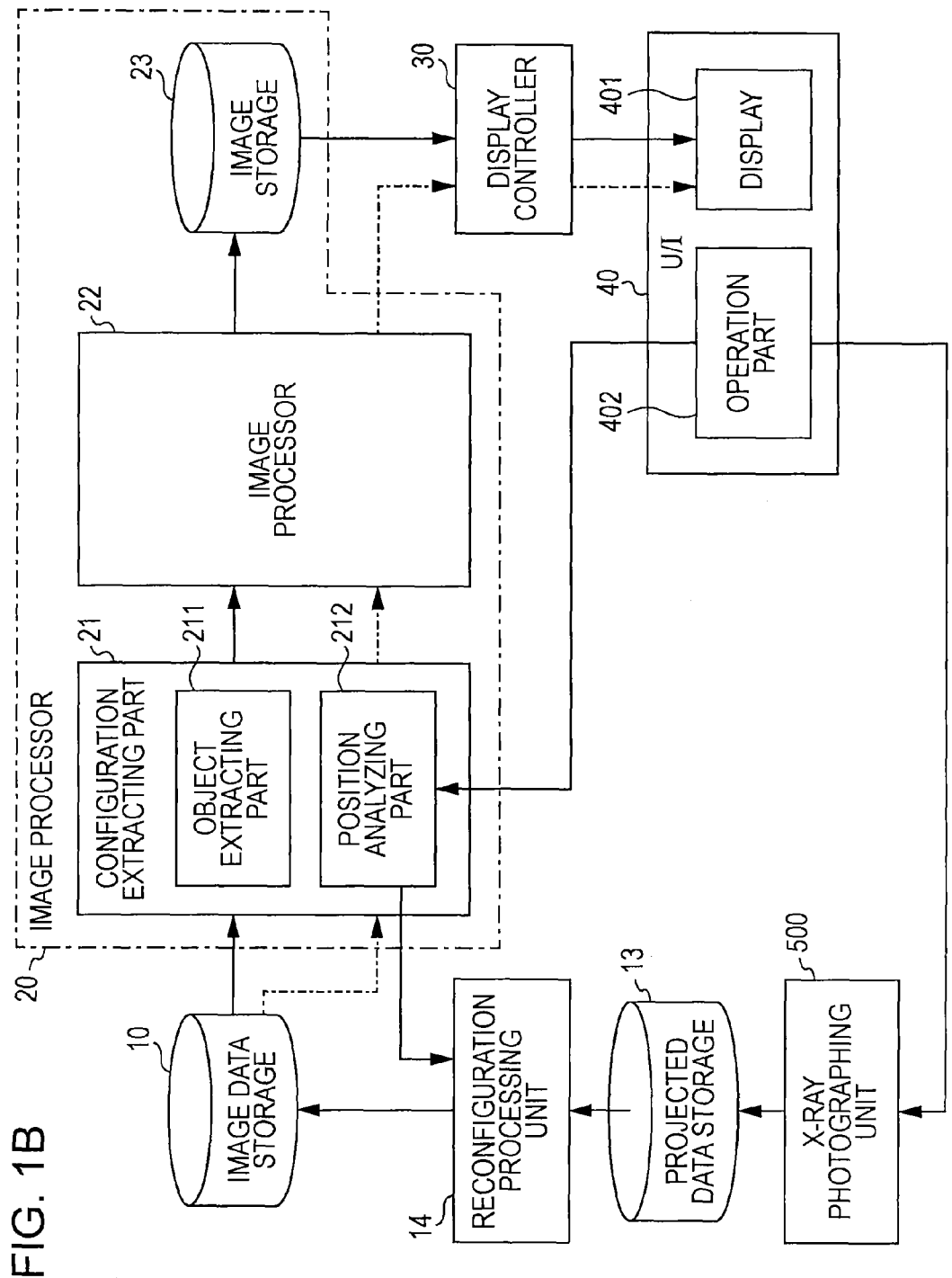
FIG. 1B is a block diagram showing the detailed configuration of the image processor.

The medical image processing apparatus according to Embodiment 1 reconstructs the projected data obtained from the X-ray CT system to generate the volume data, and generates medical images based on the volume data. Hereinafter, the configuration of the medical image processing apparatus according to the present embodiment will be described with reference to FIG. 1A and FIG. 1B together with the configuration of the X-ray CT system. As shown in FIG. 1A, the medical image displaying apparatus according to the present embodiment operates together with the X-ray photographing unit 500 (that is, the X-ray CT system), and comprises a projected data storage 13, a reconfiguration processing unit 14, an image data storage 10, an image processor 20, a display controller 30, and a U/I 40. In addition, the U/I 40 is a user interface that includes a display 401 and an operation part 402.

(X-Ray Photographing Unit 500)

The X-ray photographing unit 500 is explained as an example of the medical image processing apparatus allowing to obtain three-dimensional data in the same manner as, for example, CT, MRI, ultrasonic diagnostic equipment, etc. The X-ray photographing unit 500 comprises a gantry 1, a high-voltage generator 7, an X-ray controller 8, and a gantry/bed controller 9. The gantry 1 comprises a rotating ring 2, an X-ray source (X-ray generating unit) 3, an X-ray filter 4, an X-ray detector 5, a data accumulating unit 11, a pretreating unit 12, and a scan control 501. The X-ray detector 5 is an array type X-ray detector. That is, a channel-wise m row and a slice-wise n column of detecting elements are arranged in a matrix regarding the X-ray detector 5. The X-ray source 3 and the X-ray detector 5 are installed on the rotating ring 2, facing each other while sandwiching the test object (not illustrated) laid on a sliding bed 6. Respective channels are associated with the respective detecting elements configuring the X-ray detector 5. The X-ray source 3 faces the test object via the X-ray filter 4. When a trigger signal is supplied from the X-ray controller 8, the high-voltage generator 7 drives the X-ray source 3. The high-voltage generator 7 adds high voltage to the X-ray source 3 upon receiving the trigger signal. Thereby, X-rays are generated in the X-ray source 3 and the gantry/bed controller 9 synchronously controls the rotation of the rotating ring 2 of the gantry 1 and the slide of the sliding bed.

The scan control 501 configures a central control of all systems and controls the X-ray controller 8, the gantry/bed controller 9, as well as the sliding bed 6 based on conditions for acquiring the projected data specified in advance (hereinafter, may be referred to as the "scanning conditions"). That is, the scan control 501 rotates the rotating ring 2 along a predetermined course around the periphery of the test object while irradiating X-rays from the X-ray source 3. Furthermore, the resolution and resolving power of the projected data are determined based on the scanning conditions determined in advance. In other words, the scanning conditions are determined in advance according to the required resolution and resolving power, while the scan control 501 controls the movement of the respective parts according to the scanning conditions. By means of the resolving power of the projected data generated according to the scanning conditions (that is, the frame rate) and resolution, the maximum frame rate and resolution of the reconstructed image data is determined by the reconfiguration processing unit 14 mentioned later.

(In the Case of Changing the Scanning Conditions or the Scan Stopping Process)

Moreover, the scan control 501 is instructed from the position analyzing part 212 of the image processor 20 to change the scanning conditions or stop the processes related to acquiring the projected data (hereinafter, may be referred to as a "scan"). The image processor 20 and the position analyzing part 212 are described later. When instructions are given to change the scanning conditions, the scan control 501 changes the scanning conditions to other conditions determined in advance, which are different from the scanning conditions prior to instructions being given. Thereby, for example, before receiving instructions, the resolving power and resolution are lowered in order to acquire rough projected data, and once the instructions are received, the resolving power and resolution are increased more than before receiving instructions in order to obtain the projected data. Thereby, the rough projected data is received until instructions are received, and regarding the operation following receiving instructions (that is, the operation requiring attention), the projected data may be acquired at a level in which further careful movements may be observed. Furthermore, the projected data prior to receiving instructions may realize a resolving power and resolution allowing for analysis processing by the image processor 20 mentioned later. That is, if the conditions are satisfied, the scanning conditions may have lower resolving power and resolution settings than the scanning conditions following receiving instructions.

Moreover, when the scanning is instructed to stop, the scan control 501 controls the X-ray controller 8, the gantry/bed controller 9, and the sliding bed 6 to stop scanning. Thereby, the scan control 501 may automatically stop scanning with the instructions as the trigger.

(Commonalities in the Case of Changing the Frame Rate, Changing the Scanning Conditions, and the Scan Stopping Process)

The detected elements configuring the X-ray detector 5 may measure the strength of X-rays generated by the X-ray source 3 regarding both cases of when the test object is interpositioned between the X-ray source 3 and the detected element, and when it is not interpositioned. Accordingly, the respective detected elements measure the intensity of at least one X-ray and output an analog output signal corresponding to the intensity. The signals output from the detected element are classified into columns by time sharing in the data accumulating unit 11 and then read (that is, successively accumulated).

The data accumulating unit 11 comprises an integrated amplifier and an A/D converter. The electric signals from the respective detected element comprised in the data accumulating unit 11 are time-shared via a common integrated amplifier and then converted into digital data by the A/D converter. The data accumulating unit 11 outputs to the pretreating unit 12 the signals from the detected elements converted to digital data.

The pretreating unit 12 carries out processes such as correction by sensitivity, etc. on the digital data sent from the data accumulating unit 11, realizing the projected data. The pretreating unit 12 associates the projected data with the column, which is the read-out element of the digital data, which is the generating element thereof, and stores it in the projected data storage 13. The projected data storage 13 is the storage for storing the acquired projected data.

Furthermore, the pretreating unit 12 may supplement identification information showing the timing point (hereinafter, referred to as a "notification flag") to the projected data when instructions to change the scanning conditions are sent from the scan control 501. Thereby, the reconfiguration processing unit 14 functioning in the latter part may specify the timing point in which the scanning condition was changed within the projected data based on the notification flag.

(Reconfiguration Processing Unit 14)

The reconfiguration processing unit 14 reads out the projected data stored in the projected data storage 13. The reconfiguration processing unit 14 uses, for example, a reconstruction algorithm referred to as the Feldkamp method to back project the read project data in order to generate the image data (tomographic image data and volume data). Any method may be adopted to reconstruct the tomographic image data, such as, for example, the 2-dimensional Fourier transformation method, convolution back projection method, etc. The volume data is prepared by interpolation processing the plurality of reconstructed tomographic image data. Any method may be adopted for reconstructing the volume data such as, for example, the cone beam reconstructing method, multi-slice reconstructing method, expanded reconstructing method, etc. As mentioned above, extensive volume data may be reconstructed by means of a volume scan using an X-ray detector with many columns, as mentioned above. Moreover, when carrying out CT examination, the accumulation rate of the detected data is shortened; therefore, the reconfiguration time by the reconfiguration processing unit 14 is shortened. Accordingly, the real time image data corresponding to the scan may be prepared. Hereinafter, the volume data is referred to as "image data."

The image data according to the present embodiment is reconstructed so as to be capable of extracting bones as an example of the flexible site. The flexible site is explained exemplifying a part configured by two bones as well as a joint connecting these bones. The joint is a joint connecting the bones and including joint fluid, a synovial, and a joint capsule. Further, the side of the bone connected through the joint has cartilage and by means of this cartilage, the flexible site can be smoothly moved. In other words, this bone also includes cartilage. In addition, this flexible site comprises a plurality of construction sites, and in the above case, these construction sites include two bones to be connected by the joint. Muscles are included as an example of flexible site in addition to bones.

In this manner, the reconfiguration processing unit 14 carries out reconfiguration processing on the read projected data based on the reconstruction conditions determined in advance, and generates or reconstructs image data (that is, volume data) for each timing point based on the reconstructing conditions (that is, the predetermined volume rate). Furthermore, the timing point for reconstructing the image data is synchronized with the timing point for obtaining the projected data (that is, the resolving power related to acquiring the projected data). Specifically, a time lag is present between the timing point in which the projected data for generating the image data from the projected data is acquired and the timing point in which the image data based on the projected data corresponding with the timing is reconstructed. However, the process related to the reconstruction is at a high speed compared to the movement of the test object (for example, the activity of moving the arms and legs), and in the medical image processing apparatus related to the present embodiment, the time lag is at a level in which it is negligible. Furthermore, when the time lag is considered, the timing for carrying out the process based on the reconstructed image data (for example, process of the position analyzing part 212 mentioned later) may be adjusted based on the time lag.

Furthermore, the X-ray CT scanner related to the embodiment analyses the reconstructed image data, thereby comprehending the position and angle of the respective parts configuring an observation subject as well as the relative positional relation thereof (hereinafter, this is generally simply referred to as a "positional relation"). Therefore, the reconfiguration processing unit 14 reconstructs the image data for analysis separately from the image data for display. Specifically, the reconfiguration processing unit 14 successively reads the acquired projected data from the projected data storage 13 in parallel with the processing related to acquiring the projected data using the X-ray photographing unit 500. The reconfiguration processing unit 14 carries out reconfiguration processing on the read projected data based on the reconstruction conditions for analysis determined in advance, thereby generating the image data for analysis for each timing point based on the reconstruction conditions.

In the present embodiment, the reconstruction conditions for reconstructing the image data for analysis are configured such that the bones in the test object may be extracted from the projected data. That is, the image data is reconstructed so as to be capable of extracting bones. Furthermore, the bones also include cartilage. Moreover, the reconstruction conditions at this time are referred to as the "first conditions," and the image data generated based on the reconstruction conditions may be referred to as the "first image data." The reconfiguration processing unit 14 stores the image data for analysis successively generated for each of the timing points in the image data storage 10. The image data storage 10 is the storage for storing the image data.

Furthermore, the positional relation of components of the flexible site such as bones, etc. was described using the 2-dimensional positional relation between two bones as an example; however, the positional relation may be 3-dimensionally shaped in some cases. The example described a case when the first bone is pointing up and the second bone is pointing right, and when the second bone is pointing to the upper right with respect to this. However, a case may be considered in which the movement of the bone shifts in the rotational direction by adding a twist, etc., in addition to the movement in the 2-dimensional direction. A case may also be considered in which the position of the second bone does not move with respect to the first bone regardless of the rotation of the second bone. Accordingly, the positional relation of the components of the flexible site may be 3-dimensionally grasped, the movement in the 3-dimensional rotational direction may be obtained from among the changes in the shape characteristics of three points and the shape feature of two points, thereby the amount of change in the positional relation is also obtained regarding the twisting, and the determination process with respect to the amount of change may be carried out. The determination process itself with respect to the amount of change is the same as in the case of the 2-dimensional positional relation.

(In the Case of Changing Scanning Conditions and the Scan Stopping Process)

Moreover, the reconfiguration processing unit 14 reads the projected data from the projected data storage 13 and carries out reconfiguration processing based on the reconstruction conditions for display that have been determined in advance, thereby generating the image data for display for each timing point based on the reconstruction conditions. Furthermore, when the scanning conditions are changed while acquiring the projected data, the reconfiguration processing unit 14 may change the reconstruction conditions before and after changing the scanning conditions and reconstruct the image data for display. In this case, the reconfiguration processing unit 14 may specify the timing point at which the scanning conditions were changed based on the notification flag supplemented to the projected data. By means of operating in this manner, the reconfiguration processing unit 14 may reconstruct the image data at an increased volume rate and resolution compared to before changing regarding the image data following the change in the scanning conditions. Furthermore, hereinafter, the reconstruction conditions for display may be referred to as the "second conditions," and the image data generated based on the reconstruction conditions may be referred to as the "second image data." The reconfiguration processing unit 14 stores the image data for display that has been generated for each of the timing points in the image data storage 10.

Furthermore, the image data for display does not necessarily need to be operated in parallel with the processing related to acquiring the projected data. For example, the reconfiguration processing unit 14 may reconstruct the image data for display after acquiring a series of projected data.

Moreover, the first image data may have the reconstruction conditions allowing analysis processing by the image processor 20 mentioned later. That is, as long as the conditions are satisfied, for example, the volume rate of the first image data may be lower than the volume data at generating the image data for display. Moreover, the resolution of the first image data may be lower than the resolution of the image data for display. The processing load during analysis may be reduced by means of operating in this manner.

(In the Case of Changing the Frame Rate)

Furthermore, the reconfiguration processing unit 14 first generates image data for analysis and outputs this to the image processor 20; then, it receives the analysis results from the image processor 20 and generates image data for display. Details of the image processor 20 are described later. Detailed operations of the reconfiguration processing unit 14 are described in the following. Furthermore, the maximum volume rate and resolution of the reconstructed image data become the resolving power (that is, the frame rate) and resolution of the projected data. Accordingly, in the medical image processing apparatus related to the present embodiment, the projected data must be acquired under conditions allowing for realization of the volume rate and resolution of the image data for analysis and displaying.

The reconfiguration processing unit 14 first carries out reconfiguration processing with respect to the read projected data based on the reconstruction conditions for analysis determined in advance, and then generates image data for each timing point based on the reconstruction conditions. Furthermore, in the present embodiment, the reconstruction conditions are configured such that the bones in the test object may be extracted from the projected data. That is, the image data is reconstructed so as to be capable of extracting bones. Furthermore, the bones also include cartilage. Moreover, the image data generated based on the reconstruction conditions at this time corresponds with the "first image data." The reconfiguration processing unit 14 stores image data for analysis successively generated for each of the timing points in the image data storage 10. The image data storage 10 is the storage for storing image data. Furthermore, the first image data may have reconstruction conditions allowing for analysis processing by the image processor 20 described later. That is, if the conditions are satisfied, for example, the volume rate of the first image data may be lower than the volume data upon generation of the image data for display. Moreover, the resolution of the first image data may be lower than the resolution of the image data for display. The processing load during analysis may be reduced by means of operating in this manner.

Moreover, the reconfiguration processing unit 14 receives a notification of a time width comprising a plurality of timing points from the position analyzing part 212. The time width corresponds with a part in a series of time widths in which the first image data is generated based on the reconstruction conditions. The reconfiguration processing unit 14 carries out reconfiguration processing while changing the reconstruction conditions between the notified time width and another time width, and reconstructs the image data for display. The reconstruction conditions may be stored in the reconfiguration processing unit 14 in advance, or may be made allowing for an operator to specify via an operation part 402. For example, it is advisable to determine the reconstruction conditions such that the volume rate becomes higher than other time widths regarding the specified time width. Moreover, without limiting the volume rate, the reconstruction conditions may be determined such that, for example, the resolution of the specified time width becomes higher compared to other time frames. Furthermore, the image data generated based on the reconstruction conditions with respect to the specified time width corresponds with the "second image data." The reconfiguration processing unit 14 stores the image data for analysis successively generated for each of the timing points in the image data storage 10. By means of changing the reconstruction conditions of a part of the time width and generating the image data, for example, when observing the chronologically operating test object, the image data may be generated at a higher volume rate than other areas regarding one area in the series of operations (for example, an area requiring attention). That is, regarding the one area, the medical image may be generated and displayed at a higher frame rate than other areas based on the chronologically generated image data.

Furthermore, regarding the other time width, the first image data generated for analysis may be operated such that it may be used for display as well. For example, if the observation subject may be specified by the object extracted for analysis and the volume data is also the same, there is no need to generate the image data for display again. In such cases, the reconfiguration processing unit 14 should only reconstruct image data for display regarding the specified time width. In other words, the reconfiguration processing unit 14 should only reconstruct the second projected data as the image data for display. Moreover, the reconfiguration processing unit 14 may be operated such that it only reconstructs the image data for display regarding only the specified time width (in other words, only the specified time width becomes the display subject). The operations should be appropriately changed depending on the operation. Furthermore, the reconfiguration processing unit 14 may supplement different identifying information regarding the image data for analysis and the image data for display to the respective image data, thereby storing these in the image data storage 10 allowing for differentiation.

(Commonalities in Changing the Frame Rate, Changing the Scanning Conditions, and the Scan Stopping Process)

An X-ray CT scan is used as an example for describing the present embodiment, but an MRI scan may be used for the present embodiment instead of an X-ray CT scan. An MRI scan uses the nuclear magnetic resonance (NMR) phenomenon to magnetically activate a nuclear spin in the desired inspection part of the test object placed in the magnetostatic field using a high frequency signal of Larmor frequency, calculates the density distribution, the distribution of relaxation time, etc. based on FID (free induction decay) signals and echo signals generated along with the activation, and displays the image of any section of the test object from the measured data.

(Image Processing Unit 20)

The image processor 20 includes a configuration extracting part 21, an image processor 22, and an image storage 23.

(Configuration Extracting Part 21)

The configuration extracting part 21 includes an object extracting part 211, and a position analyzing part 212. The configuration extracting part 21 successively reads the image data for analysis, which is generated by the reconfiguration processing unit 14 at each timing point and stored in the image data storage 10, from the image data storage 10. At this time, operations by the reconfiguration processing unit 14 and operations related to reading the image data for analysis to the configuration extracting part 21 may be synchronized. The configuration extracting part 21 successively outputs the first image per read-out timing to the object extracting part 211, and instructs extraction of the object from the first image data.

Figure 2A:
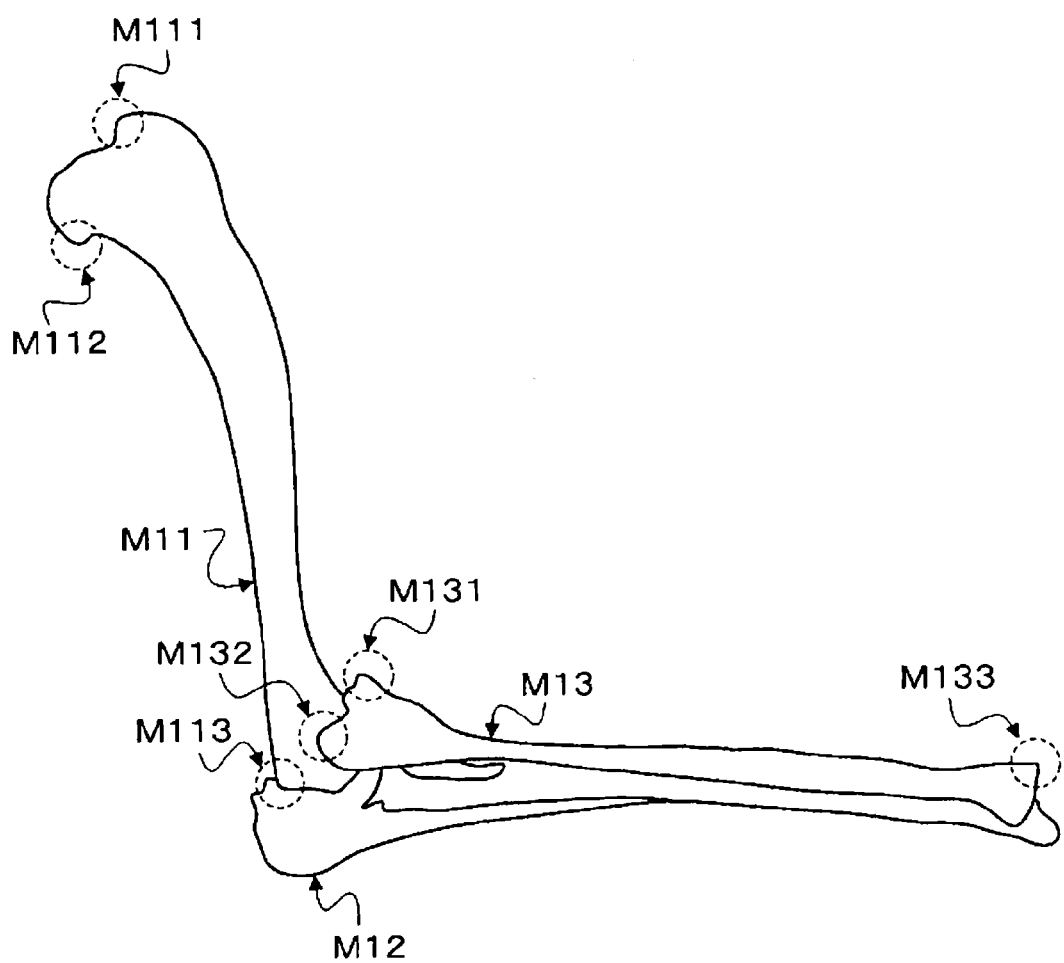
FIG. 2A explains the analysis of the positional relation in bones.

The object extracting part 211 successively receives image data for each timing point from the configuration extracting part 21. The object extracting part 211 according to the present embodiment extracts bone parts and as objects based on the voxel data in this image data. Here, FIG. 2A is referred. FIG. 2A is a diagram for explaining analysis of the positional relation in bones, and shows an example when bone objects forming arm regions are extracted. As shown in FIG. 2A, the object extracting part 211 extracts bone objects M11, M12, and M13, forming arm regions, from the first image data. In this manner, the object extracting part 211 extracts the bone objects for each of the first image data at each timing point. The object extracting part 211 outputs information indicating bone objects (for example, information indicating the form, the position, and the size of the object) extracted regarding the first image data of each timing point (in other words, extracted at each timing point) to the position analyzing part 212, while relating them with the information showing the corresponding timing. Furthermore, the object extracting part 211 corresponds to "an extracting part".

The position analyzing part 212 receives information showing the bone object at each timing point from the object extracting part 211. Or, it successively receives information showing the bone object extractor at each timing point. The position analyzing part 212 analyzes the positional relation of the bone of each timing point based on the information. A detailed example thereof is explained in the following.

The position analyzing part 212 first specifies at least two or more objects (that is, the objects subject to observation) to be used for analyzing the positional relation from among bone objects M11, M12, and M13. Specifically, for example, the position analyzing part 212 stores in advance the known bio-information of each part configuring a living body (for example, information showing the positional relation of bones configuring the upper arm and lower arm), and specifies the object based on the bio-information. Moreover, as another method, the position analyzing part 212 stores in advance the information showing the shape of the object subject to observation, and specifies the object corresponding to this shape as the object subject to observation. Hereinafter, the position analyzing part 212 is explained assuming that the objects M11 and M13 have been specified.

When the object subject for analysis M11 and M13 are specified, the position analyzing part 212 extracts at least three portions having characteristics in its shape (hereinafter, referred to as "shape characteristics") from the respective objects. For example, as shown in FIG. 2A, the position analyzing part 212 extracts the shape characteristics M111, M112, and M113 from the object M11. The position analyzing part 212 extracts the shape characteristics M131, M132, and M133 from the object M13.

Figure 2B:
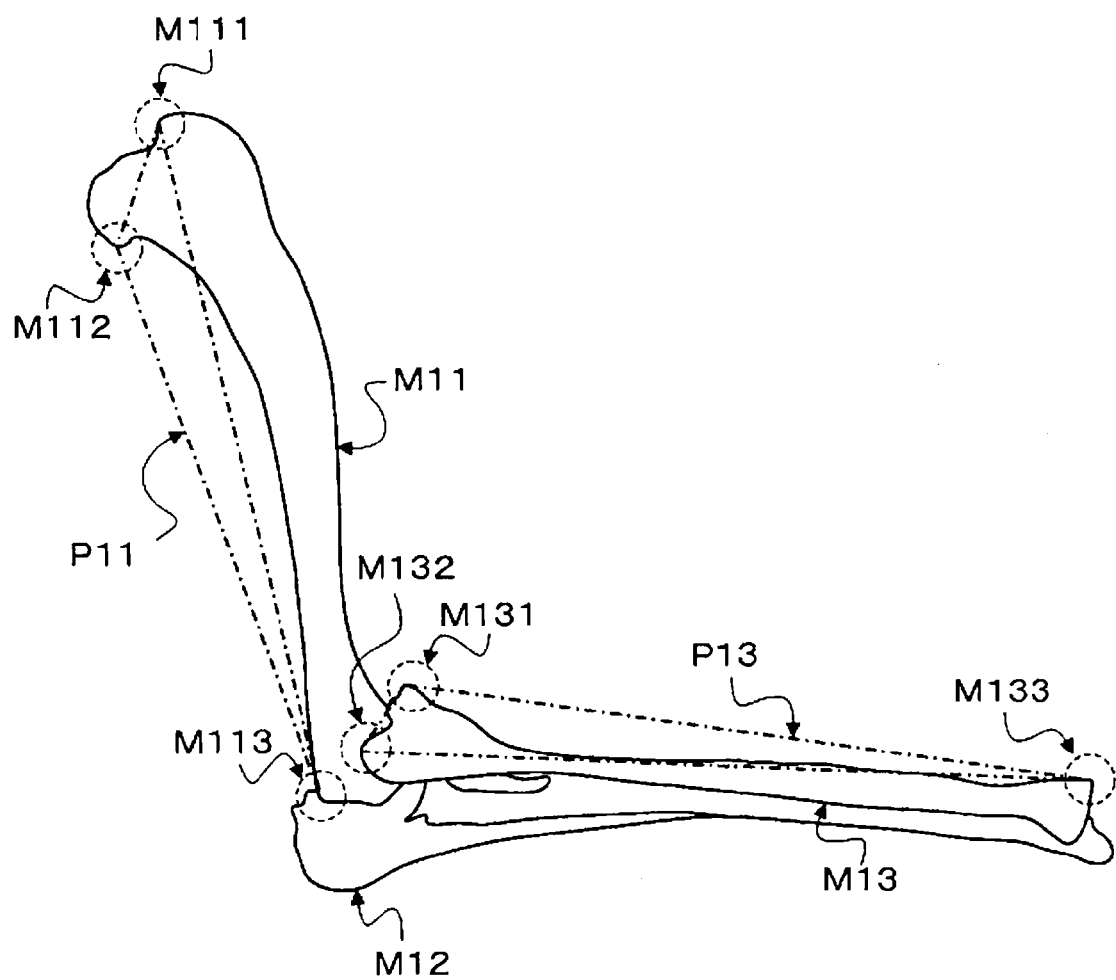
FIG. 2B explains the analysis of the positional relation in bones.

Next, the position analyzing part 212 forms planes for grasping the positions and directions of respective objects by portions (namely, points) indicating the extracted three shape characteristics, associating the plane with an object that is the origin for extracting the shape characteristics. Here, FIG. 2B will be referred. FIG. 2B is a diagram explaining the analysis of the positional relation of the bone, and shows the plane shaped based on the shape characteristics shaped from the respective objects M11 and M13. As shown in FIG. 2B, the position analyzing part 212 shapes the plane P11 by means of the shape characteristics M111, M112, and M113, and associates this with the object M11. In the same manner, the position analyzing part 212 shapes the plane P13 by means of the shape characteristics M131, M132, and M133, and associates this with the object M13.

Movement of the joint changes the position and direction of each of a plurality of bones constructing the joint and their relative positional relations (hereinafter, sometimes they are simply referred to as "positional relations"); however, the shape and the size of each bone are not changed. In other words, positional relation of the objects M11 and M13 extracted at each timing point are changed along the time sequence; however, the shape and the size of each object are not changed. The same applies to the planes P11 and P13 extracted based on the shape characteristic of each object. The position analyzing part 212 according to the present embodiment uses the characteristic and identifies the positional relation of the objects M11 and M13 based on the position and direction of the respective planes P11 and P13. Thus, by shaping the plane from each object in this manner, there is no need to carry out complicated analysis of the shape in order to grasp the position and direction of the object. Accordingly, the processing load of the position analyzing part 212 identifying the positional relation of the objects M11 and M13 may be reduced.

Figure 2C:
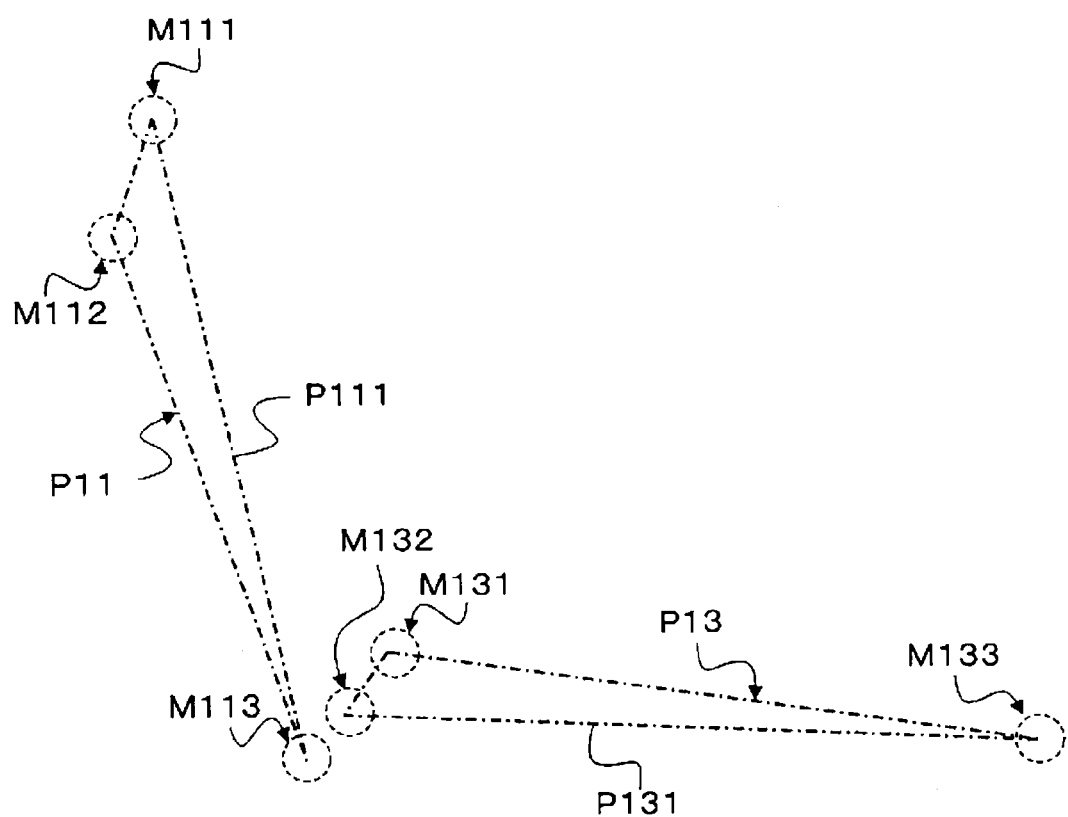
FIG. 2C explains the analysis of the positional relation in bones.

Here, FIG. 2C is referred to. FIG. 2C is a diagram explaining the analysis of the positional relation of bones, and is an example showing the positional relation of the objects M11 and M13 shown in FIG. 2A and FIG. 2B on planes P11 and P13. The position analyzing part 212 specifies the relative positional relation of the objects M11 and M13 based on the angle configured by the planes P11 and P13. Moreover, the position analyzing part 212 may specify the relative positional relation of the objects M11 and M13 based on the distance between the planes P11 and P13 by replacing the angle. Furthermore, hereinafter, the position analyzing part 212 is explained assuming that it specifies the positional relation of the objects M11 and M13 based on the planes P11 and P13.

Figure 2D:
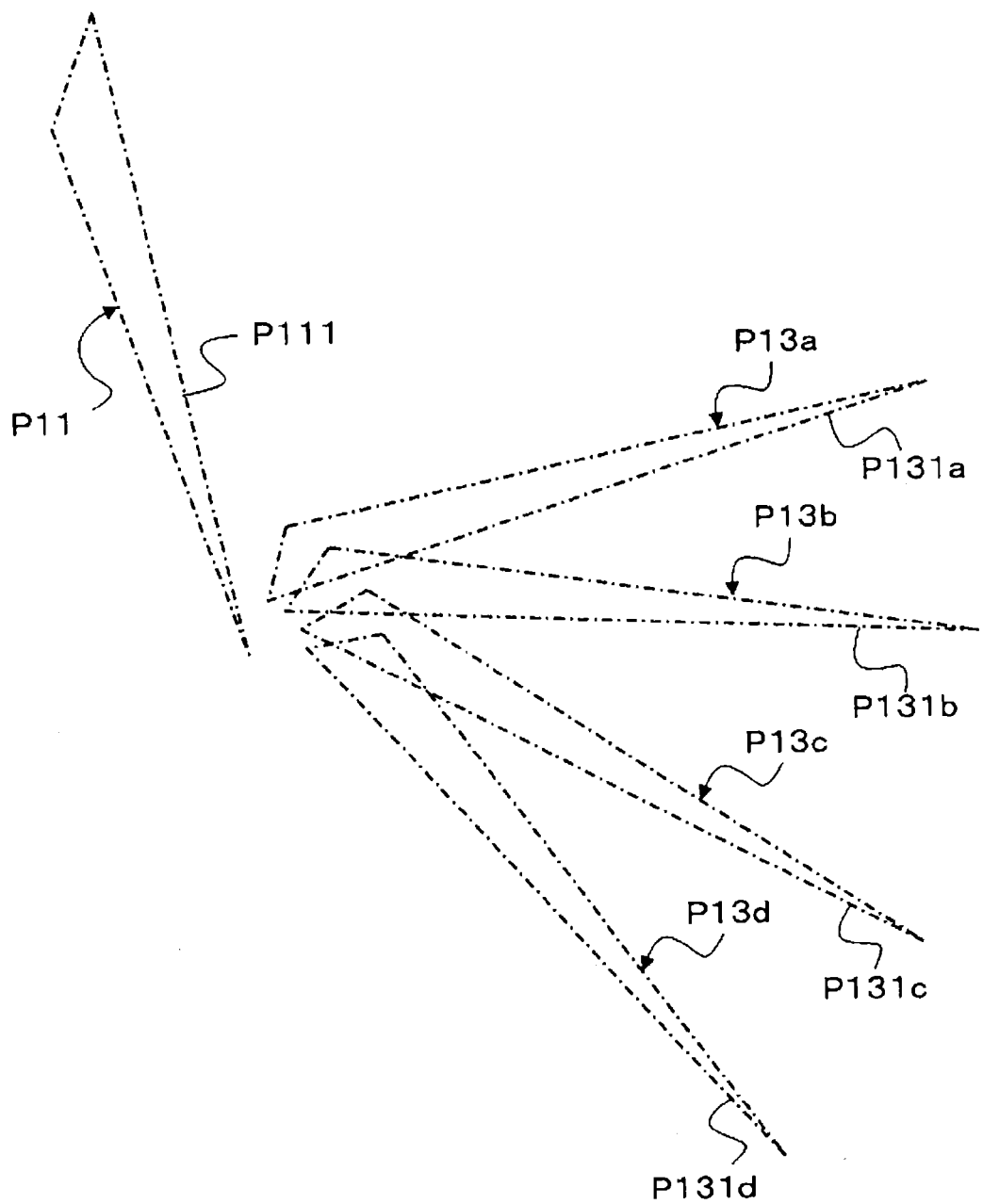
FIG. 2D explains the analysis of the positional relation in bones.

In this manner, the position analyzing part 212 specifies the positional relation of the objects M11 and M13 based on the planes P11 and P13 extracted at each timing point. Here, FIG. 2D will be referred. FIG. 2D is a diagram explaining the analysis of the positional relation of the bones and illustrates an example of the positional relation of the planes P11 and P13 at plural timing points. Furthermore, the example of FIG. 2D shows the change in position and direction of the plane P13 at each timing point assuming that the position and direction of the plane P11 (namely, the object M11) is the same, in order to make the explanation easier to comprehend. P13a to P13d in FIG. 2D are showing the plane P13 corresponding to different timing points, respectively.

In addition, the position analyzing part 212 is not limited to the above-described method based on the planes P11 and P13 if the position and direction of the standard objects M11 and M13 may be specified. For example, the position and direction of each object may be specified based on the outline of the objects M11 and M13. In this case, the position analyzing part 212 specifies a three-dimensional positional relation. Moreover, when specifying the two-dimensional positional relation, a line connecting at least two shape characteristics may be extracted from the objects M11 and M13, and the positional relation may be specified based on the two extracted lines. For example, as showing in FIG. 2C and FIG. 2D, the line P111 is extracted based on the shape characteristics M111 and M113. Moreover, the line P131 is extracted based on the shape characteristics M132 and M133. The position analyzing part 212 can identify the two-dimensional positional relation of the objects M11 and M13 from the lines P111 and P113 extracted in this manner. In addition, the position and direction may be identified by carrying out alignment of the object itself based on pixel value information from the voxel construction of an object using Mutual Information. For example, based on the distribution of the pixel value information (information showing shading), it is possible to identify the position and direction of the object (In the Case of Changing the Frame Rate)

Figure 2E:
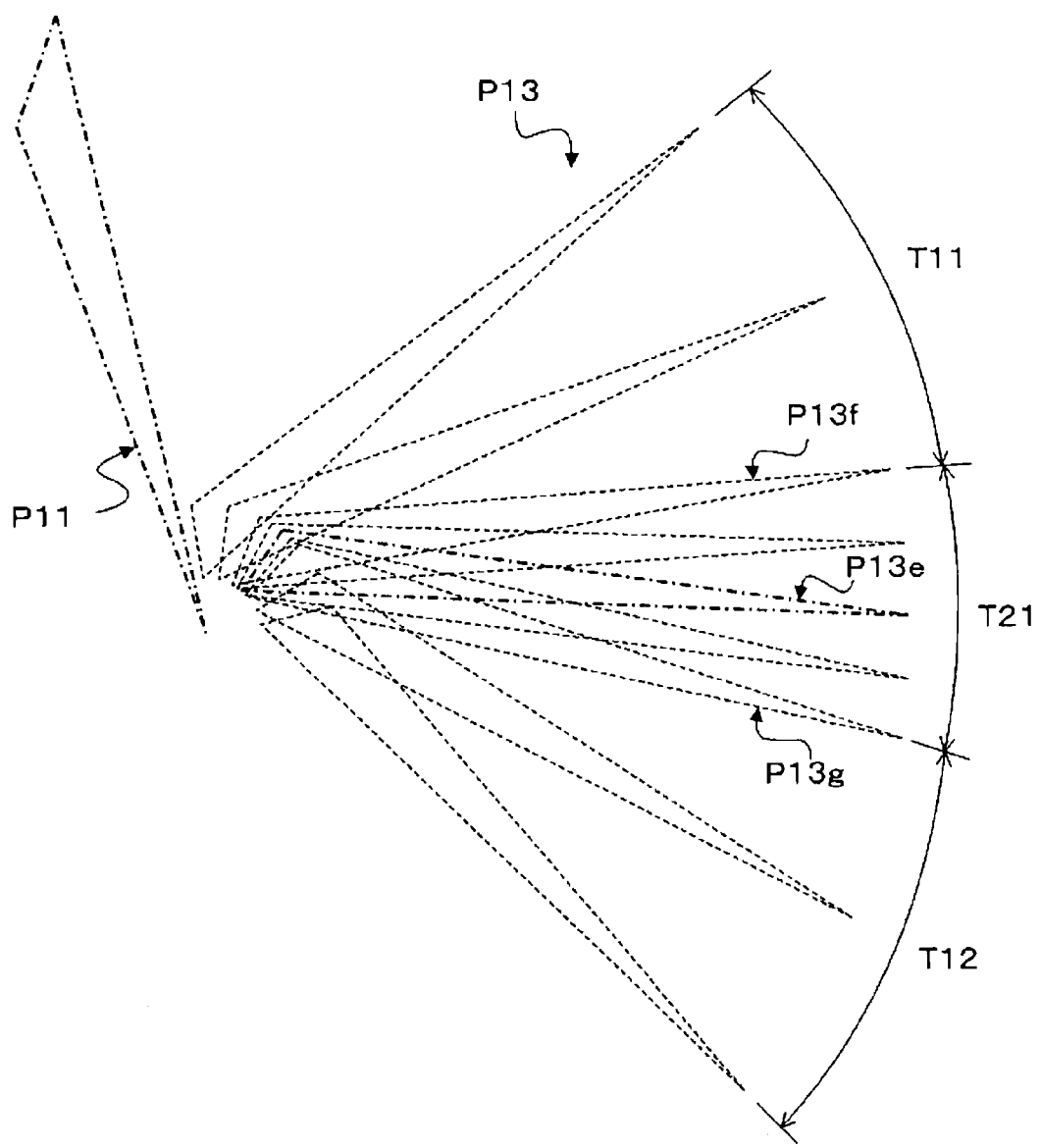
FIG. 2E explains the analysis of the positional relation in bones.

When the positional relation of the objects M11 and M13 are specified regarding a series of timing points, the position analyzing part 212 determines whether or not the specified positional relation is included in the predetermined range (satisfies the conditions determined in advance), and specifies the timing included in the range. This predetermined range may be determined in advance based on, for example, the positional relation requiring attention from among the series of movements of the observation subject. The position analyzing part 212 specifies the time width shaped by the specified timing point (in other words, the time width in which the positional relation of the objects M11 and M13 satisfy the predetermined conditions). The processing related to the specifications of the time width is explained using a detailed example in the following with reference to FIG. 2E. FIG. 2E is a diagram explaining the time width specified by the position analyzing part 212.

The planes P13e, P13f, and P13g in FIG. 2E respectively show the position of the plane P13 corresponding to the object M13 when the positional relation of the objects M11 and M13 is included in the predetermined range. That is, this indicates that in the time width T21 from the timing point corresponding to the plane P13f to the timing point corresponding to the plane P13g, the positional relation of objects M11 and M13 is included in the predetermined range. The position analyzing part 212 specifies the time width T21. Furthermore, T11 and T12 in FIG. 2E show the time widths other than the time width T21 from among the series of time widths. Furthermore, the explanations hereinafter are provided under the assumption that the position analyzing part 212 specified the time width T21 shown in FIG. 2E.

Furthermore, when the positional relation is specified based on the angle configured by the planes P11 and P13, the position analyzing part 212 determines whether or not the angle satisfies the condition of the angle determined in advance, and specifies the timing point corresponding to the angle satisfying the condition. This range may be stored in the position analyzing part 212 in advance as an absolute value.

Moreover, the position analyzing part 212 may specify the flexible range of each object based on the information showing the bone object at each timing point, and specify the relative value with respect to the flexible range. In such cases, the angle to become the standard of the range (absolute value) is stored in the position analyzing part 212 in advance. The position analyzing part 212 should specify the timing point corresponding to the standard, and specify the range of the predetermined width including the predetermined timing point. For example, if the plane P13e in FIG. 2E satisfies the condition of the angle to be the standard, the position analyzing part 212 first specifies the plane P13e. Upon doing so, the position analyzing part 212 should specify the planes P13f and P13g shaping the range of the predetermined width with the plane P13e as the standard, and specify the time width T21 shaped at the timing point corresponding to the plane.

Moreover, it is possible to specify the timing point that becomes the standard for the operator to specify the time width T21 via the operation part 402. In this case, the configuration extracting part 21 outputs the series of first image data to the image processor 22, generate medical data regarding each timing point, and display this on the display 401 via the display controller 30. The operation part 402 receives the selection of medical images to be the standard from among the displayed image data, and notifies the position analyzing part 212 regarding the timing point corresponding to the medical image. After receiving the notification, the position analyzing part 212 may specify the time width T21 based on the notified timing point.

Moreover, the timing point to become the standard for specifying the time width T21 may be specified while acquiring the projected data and supplementing the information showing the timing point in the projected data, thereby specifying the standard based on the information. Specifically, for example, reaction of the test object is monitored using external equipment such as a microphone, camera, etc. while acquiring the projected data. If reaction is detected when the test object shows a predetermined reaction (for example, uttering a voice, etc.), the information showing the timing point thereof is supplemented to the projected data. When the projected data is reconstructed to generate the first image data for analysis, the reconfiguration processing unit 14 supplements information such that it may be differentiated from other image data with respect to the image data corresponding to the timing point comprising the timing point. Thereby, the position analyzing part 212 may specify the timing point that becomes the standard for specifying the time width T21.

The position analyzing part 212 notifies the specified time width T21 to the reconfiguration processing unit 14. The reconfiguration processing unit 14 carries out reconfiguration processing while changing the reconstruction conditions between the notified time width T21 and the other time widths T11 and T12, reconstructing the image data for display for each timing point based on the reconstruction conditions. At this time, the reconfiguration processing unit 14 carries out reconfiguration processing regarding, for example, the time width T21 in which the positional relation of the objects M11 and M13 is included in the predetermined range such that the volume rate becomes higher than the other time widths T11 and T12. Thereby, the medical image may be generated and displayed at a frame rate higher than the time widths T11 and T12 regarding the time width T21. Moreover, without limiting the volume rate, the reconfiguration processing unit 14 may, for example, carry out reconfiguration processing at a higher resolution than the time widths T11 and T12 regarding the time width T21. In this manner, the reconfiguration processing unit 14 differentiates the time width T21 from other time widths T11 and T12 so as to be capable of reconstructing the image data for display under respectively different reconstruction conditions.

The reconfiguration processing unit 14 stores the series of reconstructed image data for display in the image data storage 10. Furthermore, the position analyzing part 212 corresponds to the "analyzing unit."

When analysis of the positional relation of the objects M11 and M13 regarding the series of timing points are finished in this manner and the series of reconstructed image data for display is stored in the image data storage 10, the configuration extracting part 21 reads and transfers it to the image processor 22. Furthermore the time widths T11 and T12 may be operated such that the first image data generated for analysis may also be used for display. In this case, the position analyzing part 212 only reads the second projected data corresponding to the specified time width T21 from the image data storage 10. Subsequently, the position analyzing part 212 may replace the area corresponding to the time width T21 from among the series of first image data read for analysis with the read second projected data, and transmit the series of image data to the image processor 22.

(In the Case of Changing the Scanning Conditions and the Scan Stopping Process)

When the positional relation of the objects M11 and M13 is specified, the position analyzing part 212 determines whether or not the specified positional relation becomes the predetermined positional relation. The predetermined positional relation may be determined in advance based on, for example, the positional relation corresponding to the timing point desired to control the scan from among the series of movements of the observation subject (in other words, the positional relation corresponding to the timing point at which changing the scanning condition is desired or stopping the scan is desired).

Figure 2F:
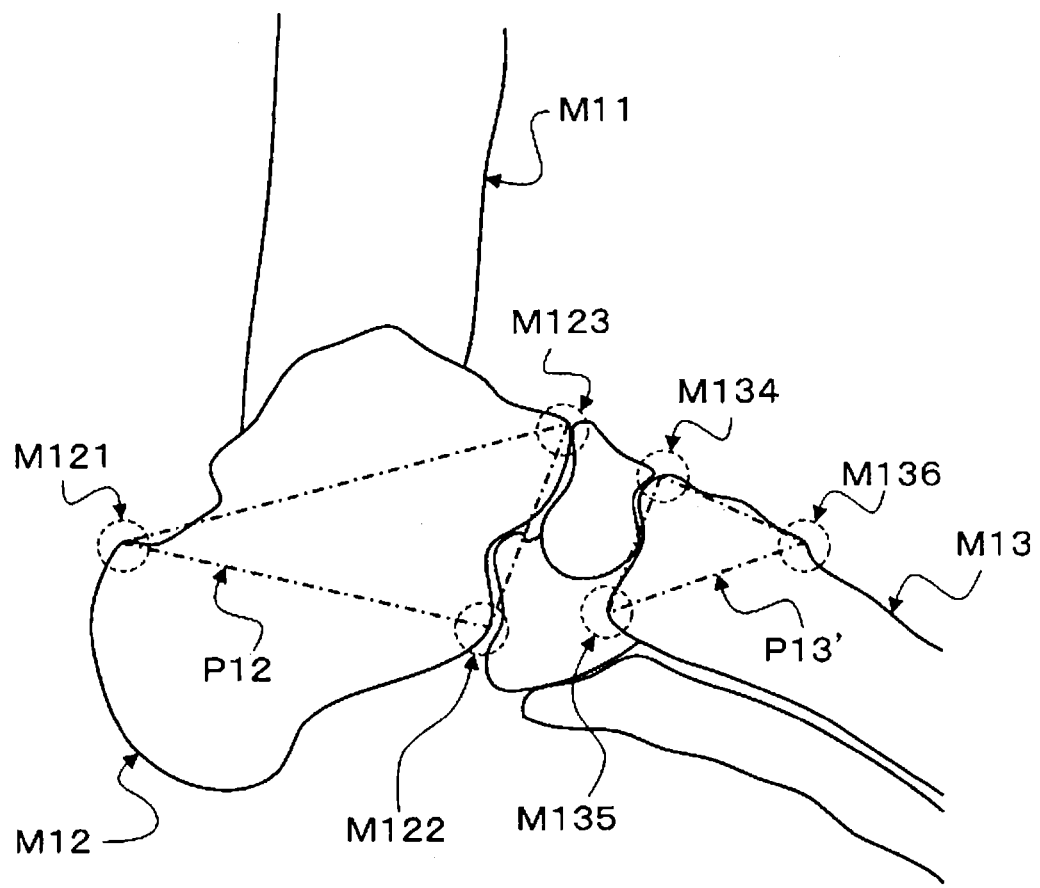
FIG. 2F explains the analysis of the positional relation in bones.
Figure 2G:
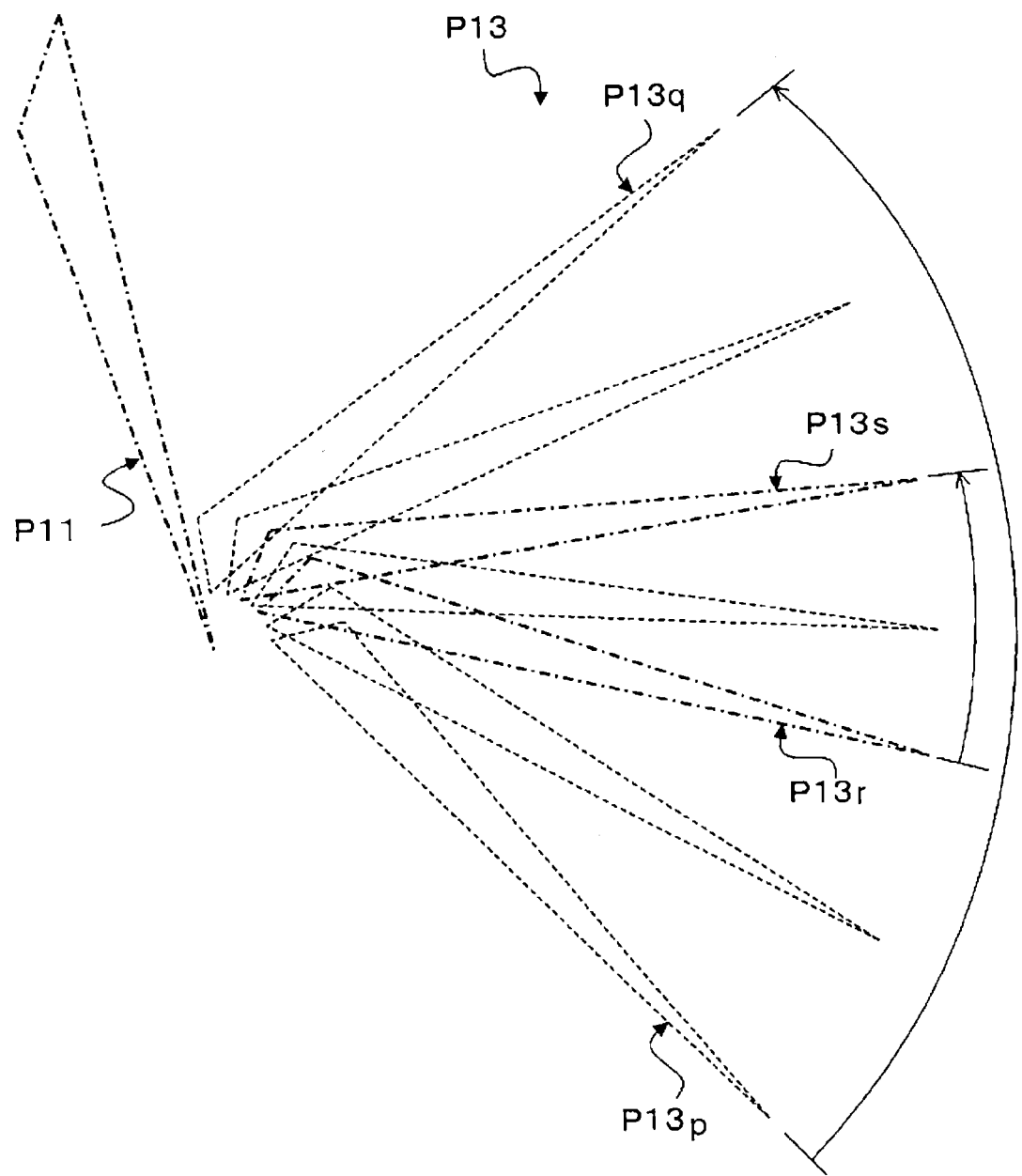
FIG. 2G explains the analysis of the positional relation in bones.

In this manner, the position analyzing part 212 successively analyzes the information showing the bone object successively output from the object extracting part 211 for each timing point, and determines whether or not the positional relation of the objects M11 and M13, which are subject for observation, satisfies the predetermined conditions. Thereby, the position analyzing part 212 detects the timing point at which the objects M11 and M13 achieve the predetermined positional relation. Furthermore, this timing point corresponds to "one timing point." When the position analyzing part 212 detects the timing point, it instructs the scan control 501 to change the scanning conditions or stop the scan. The scan control 501 receives the instructions and carries out the instructed operation (that is, change the scanning conditions or stopping the scan). Furthermore, whether changing the scanning conditions or stopping the scan is to be instructed should be associated in advance with the information showing the detected timing point (in other words, the positional relation corresponding to the timing point). A detailed example of the operation is explained in the following with reference to FIG. 2G. FIG. 2G is a diagram explaining an example of the timing point at which the position analyzing part 212 instructs the scan control 501 to change the scanning condition or stop the scan.

The planes P13p, P13q, P13r, and P13s in FIG. 2G respectively show the position of the plane P13 corresponding to the object M13 at each timing point. Specifically, the plane P13p in FIG. 2G corresponds to the timing point at which the scan is commenced. In the example of FIG. 2G, the position analyzing part 212 determines whether or not the positional relation of the objects M11 and M13 satisfy the predetermined conditions in the order of the planes P13p, P13q, P13r, and P13s. In this example, the position analyzing part 212 associates the operation related to the change in scanning conditions with the information showing the positional relation corresponding to the plane P13r, and associates the operation related to returning the changed scanning condition with the information showing the positional relation corresponding to the plane P13s. Moreover, the position analyzing part 212 associates the operation of stopping the scan with the information showing the positional relation corresponding to the plane P13r.

Thereby, scanning is commenced from, for example, the timing point corresponding to the plane P13p, and until the timing point corresponding to the plane P13r, rough projected data is obtained under the scanning conditions of low resolving power as well as resolution. The position analyzing part 212 instructs the scan control 501 to change the scanning conditions when the timing point corresponding to the plane P13r is detected. Thereby, from the timing point onwards, the projected data capable of observing detailed movements under the scanning conditions of high resolving power as well as resolution is obtained. Moreover, when the position analyzing part 212 detects the timing point corresponding to the plane P13s, it instructs the scan control 501 to change back the altered scanning conditions to the basis (that is, change the scanning conditions again). Thereby, after the timing point onwards, rough projected data is reacquired. By means of operating in this manner, projected data is obtained that is capable of observing only detailed movements regarding the area of interest from among the series of movements of the observation subject, and regarding other timing points, it may be operated such that the projected data may be acquired at a rough level. This makes it possible to reduce the processing load related to acquiring the projected data.

Moreover, when the position analyzing part 212 detects the timing point corresponding to the plane P13q, it instructs the scan control 501 to stop the scan. The scan control 501 receives the instructions and stops the operation related to acquiring the projected data (that is, the scan). By means of operating in this manner, the X-ray CT system itself may stop scanning at the timing point at which the objects M11 and M13 reach the predetermined positional relation even without the operator instructing to stop the scan.

Furthermore, the position analyzing part 212 does not necessarily need to give instructions to the scan control 501 at the detected timing. For example, the position analyzing part 212 may be operated such that it gives instructions to the scan control 501 from the detected timing point after a predetermined time has elapsed. In this manner, if it is operated such that it gives instructions to the scan control 501 based on the detected timing point, the operation of the position analyzing part 212 is not limited. Furthermore, when giving instructions to the scan control 501 at a timing point different from the detected timing point, needless to say, the timing point for giving instructions is after the detected timing point.

When the second projected data reconstructed for display is stored in the image data storage 10, the configuration extracting part 21 reads and transmits this to the image processor 22. It may also be operated such that the first image data generated for analysis is used. In this case, the position analyzing part 212 should transfer the image data for analysis that has already been read to the image processor 22.

(Commonalities in Changing the Frame Rate, Changing the Scanning Conditions, and the Scan Stopping Process)

In addition, if the positional relation of the bones can be analyzed, it is not always necessary for the whole images of respective bones such as the image of the upper arm and the lower arm to be taken as illustrated in FIGS. 2A to 2C. For example, FIG. 2F is showing the joint between the upper arm and the lower arm, and this example indicates an example in which the objects M12 and M13 are identified as the subject for analysis. In this case, the position analyzing part 212 extracts the shape characteristics M121, M122, and M123 from the object M12. Moreover, the position analyzing part 212 extracts the shape characteristics M134, M135, and M136 from the object M13. The position analyzing part 212 extracts the plane P12 shaped by the shape characteristics M121, M122, and M123, and associates this to the object M12. In the same manner, the position analyzing part 212 extracts the plane P13' shaped by the shape characteristics M134, M135, and M136, and associates this with the object M13. Hereinafter, the position analyzing part 212 identifies the positional relation of the objects M12 and M13 based on the positional relation of the planes P12 and P13'. If the position and direction of each bone and the relative positional relation may be identified in this manner based on the shape characteristics, the same process as the process mentioned above is possible even regarding cases in which the entire image of each parts are not photographed, as in FIG. 2F.

(Image Processor 22)

The image processor 22 receives the series of images reconstructed at each predetermined timing point from the configuration extracting part 21. The image processor 22 carries out image process to all image data for each timing point based on the image processing condition determined in advance, thereby respectively generating medical images.

The image processor 22 causes image storage 23 to store the generated medical images and the information indicating a timing point corresponding to image data as a generation origin while relating them with each other. The image storage 23 is storage for storing the medical images.

(Display Controller 30)

When medical images are generated for a series of timing points, the display controller 30 reads a series of medical images stored in the image storage 23. With reference to the information indicating the timing point attached to read respective medical images, the display controller 30 arranges this series of medical images along the time sequence to generate motion images. The display controller 30 causes the display 401 to display the generated motion images.

Figure 3A:
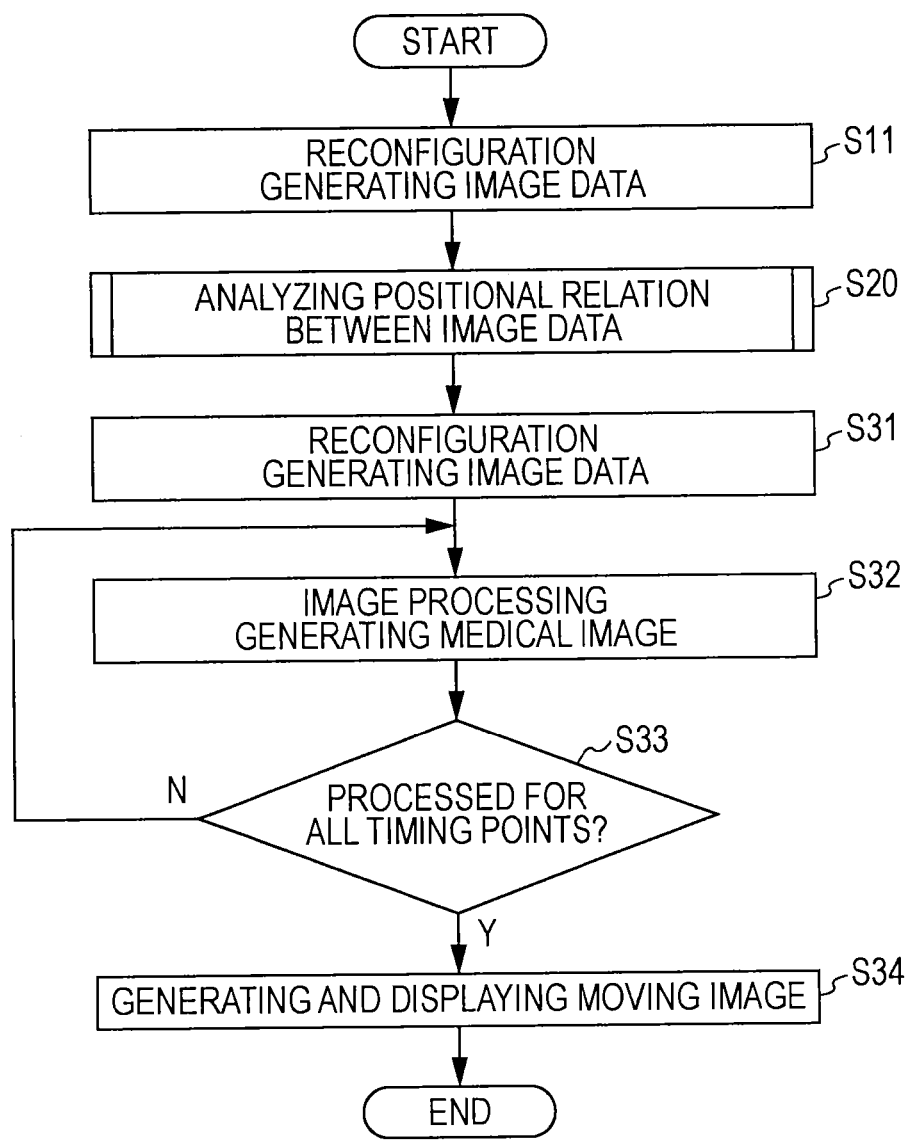
FIG. 3A is a flow chart showing a series of operations of the medical image processing apparatus pertaining to the present embodiment.
Figure 3B:
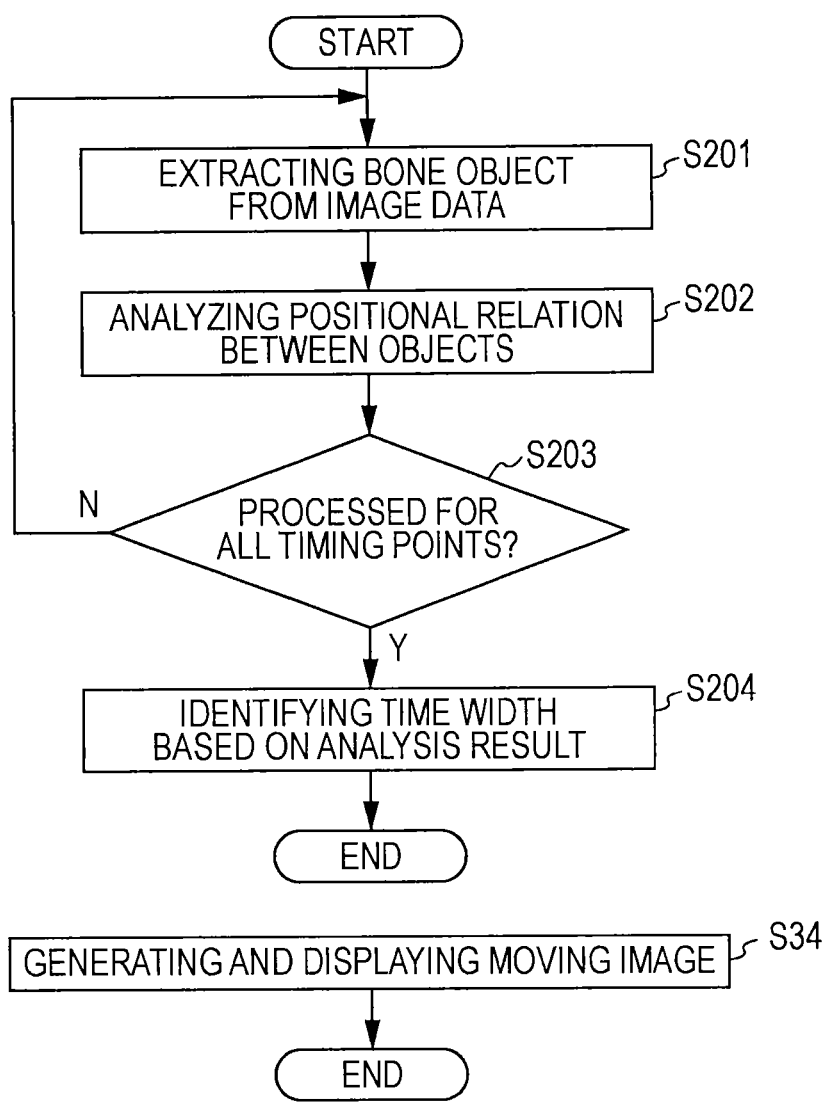
FIG. 3B is a flow chart showing the operations related to the analysis of the positional relation of Embodiment 1.

Next the series of operations of the medical image processing apparatus according to the present embodiment (related to acquiring the projected data of the X-ray CT system) is explained, with reference to FIG. 3A and FIG. 3B. FIG. 3A is a flow chart showing the series of operations of the medical image processing apparatus according to the present embodiment (related to acquiring the projected data of the X-ray CT system). Moreover, FIG. 3B is a flow chart showing the operation related to the analysis of the positional relation in the present embodiment. Furthermore, the flow chart shown in FIG. 3B corresponds to the process of step S20 of FIG. 3A.

FIG. 3A shows flow charts during the frame rate changing process. Moreover, FIG. 5 shows flow charts in the case of changing the scanning conditions and the scan stopping process. FIG. 3A and FIG. 5 correspond with each other and are explained together until S20.

(In the Case of Changing the Scanning Conditions, the Scan Stopping Process)
(Step S10)

If trigger signals are supplied from the X-ray controller 8, the high-voltage generator 7 drives the X-ray source 3. The high-voltage generator 7 applies a high voltage to the X-ray source 3 at the timing point of receiving the trigger signals. Thereby, the X-rays are generated in the X-ray source 3, and the gantry/bed controller 9 synchronously controls the rotation of the rotating ring 2 of the gantry 1 and sliding of the sliding bed 6.

The detected elements configuring the X-ray detector 5 can measure the intensities of the X-rays generated by the X-ray source 3 in both the case in which the test object is put between the X-ray source 3 and the detected element, and the case in which the test object is not put between the X-ray source 3 and the detected element. Accordingly, the respective detected elements measure at least one of the X-ray intensities, and output an analog signal corresponding to this intensity. The output signals from respective detected elements are read as distinguished for each row along the time sequence by the data accumulating unit 11 (that is, they are sequentially collected).

The data accumulating unit 11 comprises an integral amplifier and an A/D converter. Electric signals from respective detected elements included in the data accumulating unit 11 are time-divided through a common integral amplifier, then converted into digital data by the A/D converter. The data accumulating unit 11 outputs signals converted into digital data from the detected element to the pretreating unit 12.

The pretreating unit 12 carries out processing such as correction by sensitivity on the digital data to be transmitted from the data accumulating unit 11 to turn this digital data into projected data. The pretreating unit 12 causes the projected data storage 13 to store this projected data as related to a row that is a reading origin of the digital data that is a generation origin of this projected data.

(Step S11)

The reconfiguration processing unit 14 sequentially reads the obtained projected data from the projected data storage 13 in parallel with the processing for obtaining the projected data by means of the X-ray photographing unit 500. The reconfiguration processing unit 14 carries out reconfiguration processing on this read projected data based on conditions predetermined for analysis in advance, thereby generating image data for analysis for each timing point based on these reconstruct conditions.

According to the present embodiment, reconstruction conditions for reconstructing image data for analysis are configured so as to be capable of extracting the bones in the test object from the projected data. In other words, this image data is reconstructed so as to be capable of extracting the bones. Sometimes, the reconstruct conditions in this case are referred to as "first conditions" and image data generated based on these reconstruction conditions is referred to as "first image data." The reconfiguration processing unit 14 causes the image data storage 10 to store image data for analysis sequentially generated for each timing point.

(Commonalities in the Case of Changing the Frame Rate, Changing the Scanning Conditions, the Scan Stopping Process)
(Step S11)

At first, FIGS. 3A and 5 will be referred. The reconfiguration processing unit 14 reads the projected data stored in the projected data storage 13. At first, the reconfiguration processing unit 14 carries out reconfiguration processing on the read projected data based on the predetermined reconstruction conditions for analysis and generates first image data for each timing point based on these reconstruction conditions. The reconfiguration processing unit 14 causes the image data storage 10 to store this first image data generated for each timing point. Further, the first image data may be reconstruction conditions capable of carrying out analysis processing by means of an image processing unit 20 (to be described later). In other words, if these conditions are satisfied, for example, the volume rate of the first image data may be lower than the volume rate upon generating image data for display. In addition, resolution of the first image data may be lower than the resolution of the image data for display. Due to this operation, it becomes possible to reduce the processing load upon analysis.

(Step S201)

Next, FIG. 3B will be referred. At first, a configuration extracting part 21 reads the first image data reconstructed for analysis for each timing point. Alternatively, the configuration extracting part 21 sequentially reads the image data for analysis generated by the reconfiguration processing unit 14 for each timing point and stored in the image data storage 10 from the image data storage 10. In this case, the operation by means of the reconfiguration processing unit 14 and the operation according to reading of the image data for analysis by means of the configuration extracting part 21 may be synchronized with each other. The configuration extracting part 21 outputs each of the first image data for each read timing point to an object extracting part 211, providing instructions to extract the object.

The object extracting part 211 sequentially receives the first image data for each timing point from the configuration extracting part 21. According to the present embodiment, the object extracting part 211 extracts bone parts as the objects based on the voxel data in this first image data. Here, FIG. 2A will be referred. FIG. 2A is a view for explaining analysis of the positional relationship in bones, and illustrates an example when bone objects forming arm regions are extracted. As illustrated in 2A, the object extracting part 211 extracts bone objects M11, M12, and M13, forming arm regions from the first image data. Thus, the object extracting part 211 extracts the bone objects for each of the first image data at each timing point. The object extracting part 211 outputs information indicating bone objects (for example, information indicating the form, the position, and the size of the object) extracted from each timing point (in other words to the position analyzing unit 212, extracted at each timing point) as related to information indicating the corresponding timing point.

(Step S202)

The position analyzing unit 212 receives information indicating the bone objects from the object extracting part 211 for each timing point. The position analyzing unit 212 identifies at least two or more objects used for analysis of the positional relationship (that is, the analysis object) among bone objects M11, M12, and M13. Alternatively, the position analyzing unit 212 sequentially receives the information indicating the bone objects extracted for each timing point from the object extracting part 211. The position analyzing unit 212 sequentially analyzes the positional relationship of the bones based on this information. Hereinafter, an explanation will be provided assuming that the position analyzing unit 212 identifies the objects M11 and M13.

At first, the position analyzing unit 212 identifies at least two or more objects used for analysis of the positional relationship (that is, the analysis object) among the bone objects M11, M12, and M13. Specifically, for example, the position analyzing unit 212 stores the biological body information of respective parts constructing the known biological body (for example, the information indicating the positional relationship of the bones comprising the brachial region and the antebrachial region) and it identifies an object based on this biological body information. In addition, as another method, the position analyzing part 212 stores the information indicating the shape of the observation object in advance and identifies an object coinciding with this shape as the analysis object. Hereinafter, this will be described assuming that the position analyzing unit 212 identifies the objects M11 and M13.

If the analysis objects M11 and M13 are identified, the position analyzing unit 212 extracts at least three points having features in its shape (hereinafter, referred to as "shape features") from each of these objects. For example, as illustrated in FIG. 2A, the position analyzing unit 212 extracts shape features M111, M112, and M113 from the object M11. The position analyzing unit 212 extracts the shape features M131, M132, and M133 from the object M13.

Next, the position analyzing part 212 forms planes for grasping the positions and directions of respective objects by simulation by portions (namely, points) indicating the extracted three points of shape features, relating the plane with the object that is the origin for extracting the shape features. Here, FIG. 2B will be referred. FIG. 2B is a view explaining the analysis of the positional relationship of the bones, indicating a plane formed based on the shape features formed by each of the objects M11 and M13. As illustrated in FIG. 2B, the position analyzing unit 212 forms a plane P11 due to the shape features M111, M112, and M113 and relates this to the object M11. In the same way, the position analyzing unit 212 forms a plane P13 due to the shape features M131, M132, and M133 and relates this to the object M13.

When the joint is moved, the position and direction of each of a plurality of bones comprising the joint and their relative positional relationships (hereinafter, they are simply referred to as the "positional relationship") are changed; however, the shape and size of each bone are not changed. In other words, the objects M11 and M13 extracted at each timing point are changed in the positional relationship at each timing point; however, the shape and size of each object are not changed. The same applies to the planes P11 and P13 extracted based on the shape feature of each object. According to the present embodiment, using this feature, the position analyzing unit 212 identifies the positional relationships of the objects M11 and M13 based on the position and direction of each of the planes P11 and P13. Thus, by forming a plane from each object, there is no need to carry out analysis of a complete shape in order to grasp the position and direction of the object, making it possible to reduce the processing load. Therefore, the position analyzing unit 212 can reduce the processing load for identifying the positional relationships of the objects M11 and M13.

Here, FIG. 2C will be referred. FIG. 2C is a view explaining the analysis of the positional relationship of bones and illustrates an example in which the positional relationship between the objects M11 and M13 illustrated in FIG. 2A and FIG. 2B is represented by planes P11 and P13. The position analyzing unit 212 identifies the relative positional relationship between the objects M11 and M13, for example, based on the angle formed by the planes P11 and P13. In addition, the position analyzing unit 212 may identify the relative positional relationship between the objects M11 and M13 based on the distance between the planes P11 and P13 in place of the angle. Hereinafter, this will be described assuming that the position analyzing unit 212 identifies the positional relationship between the objects M11 and M13 based on P11 and P13.

Here, FIG. 2D will be referred. FIG. 2D is a view explaining the analysis of the positional relationship of the bones and illustrates an example of the positional relationship between the planes P11 and P13 at a plurality of timing points. According to the example of FIG. 2D, in order to simplify the explanation, assuming that the position and direction of the plane P11 (that is, the object M11) are not changed, the position and direction of the plane P13 for each timing point are illustrated. P13a to P13d in FIG. 2D illustrates the plane P13 corresponding to different timing points, respectively.

When the positional relationship between the object M11 and M13 is identified, the position analyzing unit 212 determines whether or not the identified positional relationship is a specific positional relationship. This specific positional relationship may be decided in advance, for example, based on the positional relationship corresponding to a timing point desiring to control the scan in a series of movements in the observation object (in other words, the positional relationship corresponding to a timing point desired to change the scanning conditions, or desired to stop the scan).

As described above, in the event of changing the frame rate, the processing common to the case of changing the scanning conditions and the case of scan stopping processing have been described. Hereinafter, respective cases will be separately explained.

(In the Case of Changing the Frame Rate)
(Step S203)

Thus, based on the planes P11 and P13 extracted at each timing point, the position analyzing unit 212 identifies the positional relationship between the objects M11 and M13 at each timing point thereof. When a timing point that does not identify the positional relationship between the objects M11 and M13 exists (Step S203, N), the position analyzing unit 212 identifies the positional relationship between the objects M11 and M13 with respect to the timing point.

(Step S204)

When the positional relationship between the objects M11 and M13 is identified with respect to a series of timing points (Step S203,Y), the position analyzing unit 212 determines whether or not the identified positional relationship is included in a specific range (whether or not it satisfies a predetermined condition), identifying the timing point included in the range. This specific range may be predetermined, for example, based on a positional relationship to be focused on in a series of movements of the observation object. The position analyzing unit 212 identifies a time width formed by the identified timing point (in other words, a time width in which the positional relationship between the objects M11 and M13 satisfies specific conditions). In the following descriptions, the position analyzing unit 212 will be explained assuming that a time width T21 illustrated in FIG. 2E is identified. The position analyzing unit 212 notifies the reconfiguration processing unit 14 of the identified time width T21.

(Step S31)

Here, FIG. 3A will be referred. The reconfiguration processing unit 14 reconstructs the image data for display for each timing point based on reconstruction conditions while altering the reconstruction conditions between the notified time width T21 and other time widths T11 and T12, and carrying out reconfiguration processing. The reconfiguration processing unit 14 causes the image data storage 10 to store the reconstructed series of image data for display.

Thus, if analysis of the positional relationship of the objects M11 and M13 with respect to a series of timing points is completed and the reconstructed series of image data for display is stored in the image data storage 10, the configuration extracting part 21 reads these image data and transfers them to an image processor 22.

(Step S32)

The image processor 22 receives the reconstructed series of image data for each specific timing point from the configuration extracting part 21. The image processor 22 generates medical images respectively by subjecting each of the image data for each timing point to image processing based on predetermined image processing conditions. The image processor 22 causes the image storage 23 to store the generated medical images and the information indicating a timing point corresponding to image data as a generation origin while relating them with each other.

(Step S33)

Thus, the image processor 22 generates medical images by subjecting the image data corresponding to each timing point to image processing. When timing point with no medical images generated exists (Step S33, N), the image processor 22 generates medical images with respect to this timing point.

(Step S34)

When medical images are generated for a series of timing points (Step S33,Y), the display controller 30 reads a series of medical images stored in the image storage 23. With reference to the information indicating the timing point attached to read respective medical images, the display controller 30 arranges this series of medical images along the time sequence to generate motion images. The display controller 30 causes the display 401 to display the generated motion images.

As described above, according to the present embodiment, the medical image processing apparatus analyzes changes in the positional relationship of at least two sites that temporarily work with each other by means of the bone objects corresponding to these sites, the sites being related to a surgery site of muscles, tendons or bones such as a joint and a spondylus. Moreover, the medical image processing apparatus identifies a time width having a positional relationship of the bone objects corresponding to these sites included in a specific range and reconstructs image data for display by changing the reconstruction conditions in this time width and other time widths in addition to carrying out reconfiguration processing. Thereby, the medical image processing apparatus according to the present embodiment can display medical images at a frame rate higher than other time widths with respect to a time width having a positional relationship of two or more sites included in a specific range.

(In the Case of Changing the Scanning Conditions, the Scan Stopping Process)
(Step S31)

Thus, the position analyzing unit 212 sequentially analyzes the information indicating the bone objects to be sequentially output from the object extracting part 211 for each timing point, and determines whether or not the positional relationship of the objects M11 and M13 that are observation objects satisfies specific conditions. Thereby, the position analyzing unit 212 detects a timing point wherein the objects M11 and M13 have a specific positional relationship. This timing point corresponds to "one timing point."

(Step S32)

If the position analyzing unit 212 detects this timing point (Step S31, Y), it instructs the scan control 501 to control the operation according to the scan (that is, it changes the scanning conditions or stops scanning). When this timing point is not detected (Step S31, N), the position analyzing unit 212 shifts to the next process without providing instructions to control operation of the scan to the scan control 501.

(Step S33)

The X-ray CT system according to the present embodiment carries out the above-described series of processing unless the operator instructs the completion of imaging (Step S33, N). If the operator instructs the completion of imaging (Step S33, Y), the X-ray CT system according to the present embodiment terminates the process for obtaining the projected data, in addition to terminating the analysis processing for controlling this.

As described above, the X-ray CT system according to the present embodiment analyzes changes in the positional relationship of at least two or more sites constructing flexible sites in accordance with the bones corresponding to these sites, the flexible sites being related to a surgery site of muscles, tendons or bones such as a joint and a spondylus. Moreover, the X-ray CT system detects a timing point in which the positional relationship of the bone objects corresponding to these sites satisfies specific conditions, and it controls the operation for acquiring projected data based on this timing point (that is, it changes the scanning conditions or stops scanning). Thereby, in the X-ray CT system according to the present embodiment, the X-ray CT system itself can automatically control the operation for acquiring projected data without the operator when the positional relationship of two or more sites satisfies specific conditions.

According to the above-described embodiments, as a flexible site, bones and joints are exemplified; however, as a flexible site, it is also possible to focus on cartilage. In the above-described embodiments, three points of shape features regarding the bones have been identified; however, for example, by identifying three points of shape features regarding cartilage and two shape features, the above-described processing can also be carried out. As a merit of analyzing cartilage as a flexible site in place of a bone, improved diagnosis accuracy of disc hernias can be cited. Disc hernias occur due to protrusion of cartilage in the joints.

Acquiring image data of cartilage by means of a medical imaging apparatus, the positional relationship of cartilage is analyzed as well as the above-described positional relationship of the bones. Depending on the analysis result, it is possible to determine whether or not cartilage protrudes. If cartilage protrudes, disc hernias occur, allowing a diagnosis to be made without waiting for analyses regarding the bones. This analysis processing can be carried out in place of analysis processing regarding the bones; however, the analysis processing can be carried out together with analysis processing regarding the bones. When acquisition and analysis of images are carried out in parallel with processing of the bones and it is found that a disk hernia has occurred from analysis results regarding images of the cartilage, by completing analysis without waiting for analysis of the bones, it is possible to acquire an accurate diagnosis at an early stage. Further, other than the case in which cartilage protrudes, the case in which cartilage is crushed by sites such as other bones is also considered. When cartilage is crushed more than a certain extent, crushing of the cartilage is defined as an analysis result, and based on this result, it is possible to change the frame rate, or the processing can shift to changing of the scanning conditions or stopping of the scan.

Second Embodiment

Next, a medical image displaying apparatus according to a second embodiment will be described. In the medical image displaying apparatus according the first embodiment, the time width to change the reconstruction conditions based on the positional relationship of the bone objects, and the timing point for controlling the operation for acquiring projected data are identified. In the medical image processing apparatus according to the present embodiment, the time width to change the reconstruction conditions based on changes in the outline of the test object, and the timing point for controlling the operation for acquiring projected data are identified. The medical image processing apparatus according to the present embodiment will be described below focusing on different points from the first embodiment.
(In the Case of Changing the Frame Rate)

At first, the reconfiguration processing unit 14 according to the present embodiment carries out reconfiguration processing on the read projected data based on the predetermined reconstruction conditions for analysis, then generates image data for each timing point based on these reconstruction conditions. Further, in the present embodiment, these reconstruction conditions are configured so as to be capable of extracting the surface layer of the test object from the projected data (that is, skin). Specifically, these reconstruction conditions have a range of CT numbers that is the target of reconstruction and which is adjusted at a level capable of extracting the surface layer. Thereby, this image data is reconstructed so as to be capable of extracting the surface layer. Image data generated based on the reconstruction conditions in this case correspond to the "first image data." The reconfiguration processing unit 14 causes the image data storage 10 to store image data generated for each timing point. Such extraction of the surface layer of the test object from image data makes it possible to identify the outline of the test object based on the extracted surface layer. In the present embodiment, by analyzing shape change in the outline of the test object at a plurality of timing points based on the surface layer of the test object thus reconstructed, reconstruction conditions of image data for display are changed depending on whether or not the shape of the outline thereof is included within the specific range.

Further, processing for reconstructing image data for display by the reconfiguration processing unit 14 according to the present embodiment is identical with the operation of the reconfiguration processing unit 14 according to the first embodiment. In other words, the reconfiguration processing unit 14 receives notification of a time width T21 including a plurality of timing points from the position analyzing unit 212. The reconfiguration processing unit 14 carries out reconfiguration processing while changing the reconstruction conditions in the notified time width T21, and other time widths T11 and T12, then reconstructs image data for display to cause the image data storage 10 to store the reconstructed image data.
(In the Case of Changing the Scanning Conditions, the Scan Stopping Process)

The X-ray CT system according to the present embodiment grasps the position and direction of respective sites configuring the observation object and the relative positional relationship thereof (hereinafter, it is simply referred to as the "positional relationship") by analyzing the reconstructed image data. Therefore, the reconfiguration processing unit 14 reconstructs image data for analysis separately from the image data for display. Specifically, the reconfiguration processing unit 14 sequentially reads the acquired projected data from the projected data storage 13 in parallel with processing for acquiring projected data by means of the X-ray photographing unit 500. The reconfiguration processing unit 14 generates image data for analysis for each timing point based on these reconstruction conditions by carrying out reconfiguration processing on this read projected data based on the predetermined reconstruction conditions for analysis.

According to the present embodiment, the reconstruction conditions for reconstructing the image data for analysis are configured so as to be capable of extracting the surface layer of the test object from the projected data (that is, skin). Specifically, these reconstruction conditions have a range of CT numbers that are the target of reconstruction, with a range that is adjusted at a level capable of extracting the surface layer. Thereby, this image data is reconstructed so as to be capable of extracting the surface layer. The reconstruction conditions in this case correspond to "first conditions" according to the present embodiment, and the image data generated based on these reconstruction conditions correspond to the "first image data." The reconfiguration processing unit 14 causes the image data storage 10 to store the image data generated for each timing point. Such extraction of a surface layer of the test object from image data makes it possible to identify the outline of the test object based on the extracted surface layer. In the present embodiment, by analyzing shape change in the outline of the test object along a time sequence based on the surface layer of the test object thus reconstructed, the timing point of controlling the operation for obtaining the projected data is identified depending on whether or not the shape of the outline thereof satisfies specific conditions.

Further, processing for reconstructing image data for display by the reconfiguration processing unit 14 according to the present embodiment is identical with operation of the reconfiguration processing unit 14 according to the first embodiment. In other words, the reconfiguration processing unit 14 generates image data for display for each timing point based on these reconstruction conditions by reading the projected data from the projected data storage 13 and carrying out the reconfiguration processing based on predetermined reconstruction conditions for display. Hereinafter, sometimes reconstruction conditions for display are referred to as "second conditions" and the image data generated based on these reconstruction conditions is referred to as "second projected data." The reconfiguration processing unit 14 causes the image data storage 10 to store this image data for display generated for each timing point.

The image data for display does not always need to be operated in parallel with the processing for obtaining projected data. For example, the reconfiguration processing unit 14 may reconstruct the image data for display after a series of projected data is obtained. This operation is also identical with the first embodiment.

The configuration extracting part 21 (in the case of changing the frame rate) reads the first image data reconstructed for analysis for each timing point. The configuration extracting part 21 outputs each of the read first image data for each timing point to the object extracting part 211, and instructs it to extract the object. This operation of the configuration extracting part 21 is identical with the first embodiment.

The configuration extracting part 21 (in the case of changing the scanning conditions or the scan stopping process) sequentially reads the image data for analysis sequentially generated by the reconfiguration processing unit 14 for each timing point stored in the image data storage 10 from the image data storage 10. In this case, the operation by the reconfiguration processing unit 14 and the operation for reading the image data for analysis by the configuration extracting part 21 may be synchronized with each other. The configuration extracting part 21 sequentially outputs the read first image data object for each timing point to the object extracting part 211, and instructs it to extract the object from the first image data. The operation of this configuration extracting part 21 is the same as the first embodiment.

(Common to the Cases of Changing the Frame Rate, Changing the Scanning Conditions, and the Scan Stopping Process)

Figure 4A:
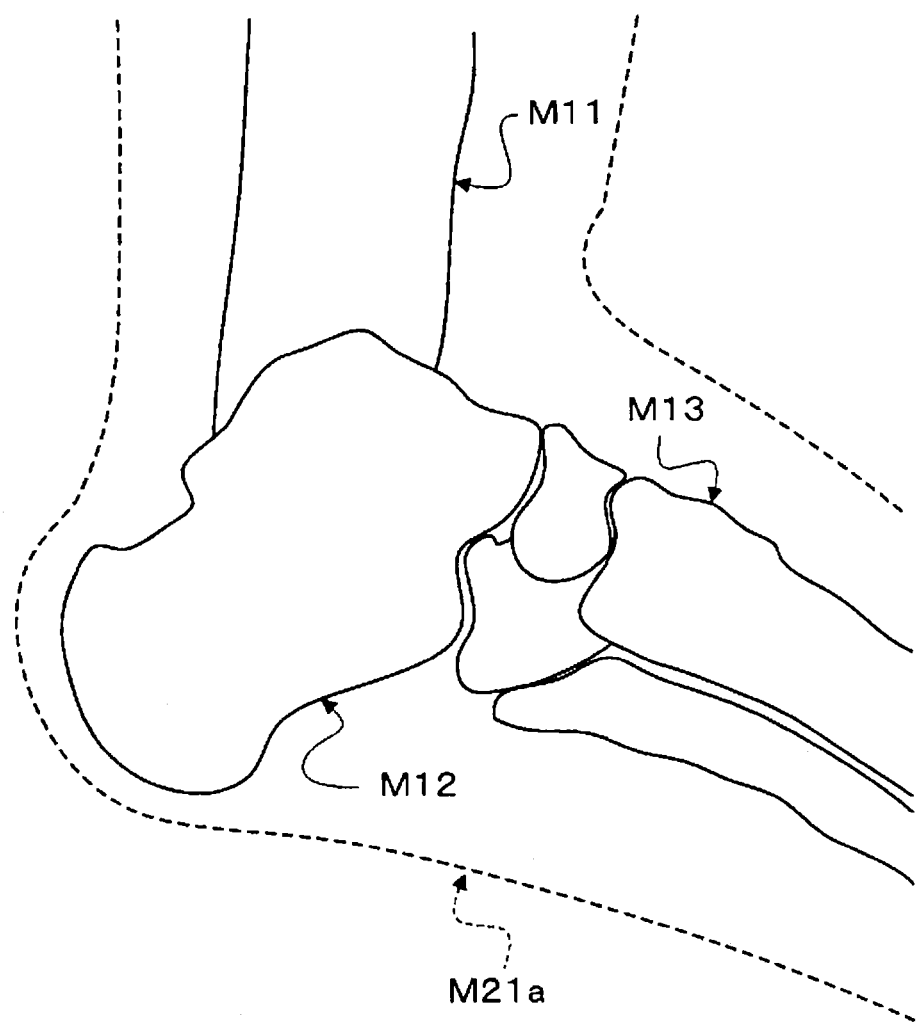
FIG. 4A explains the analysis of the shape based on the surface layer of the test object.
Figure 4B:
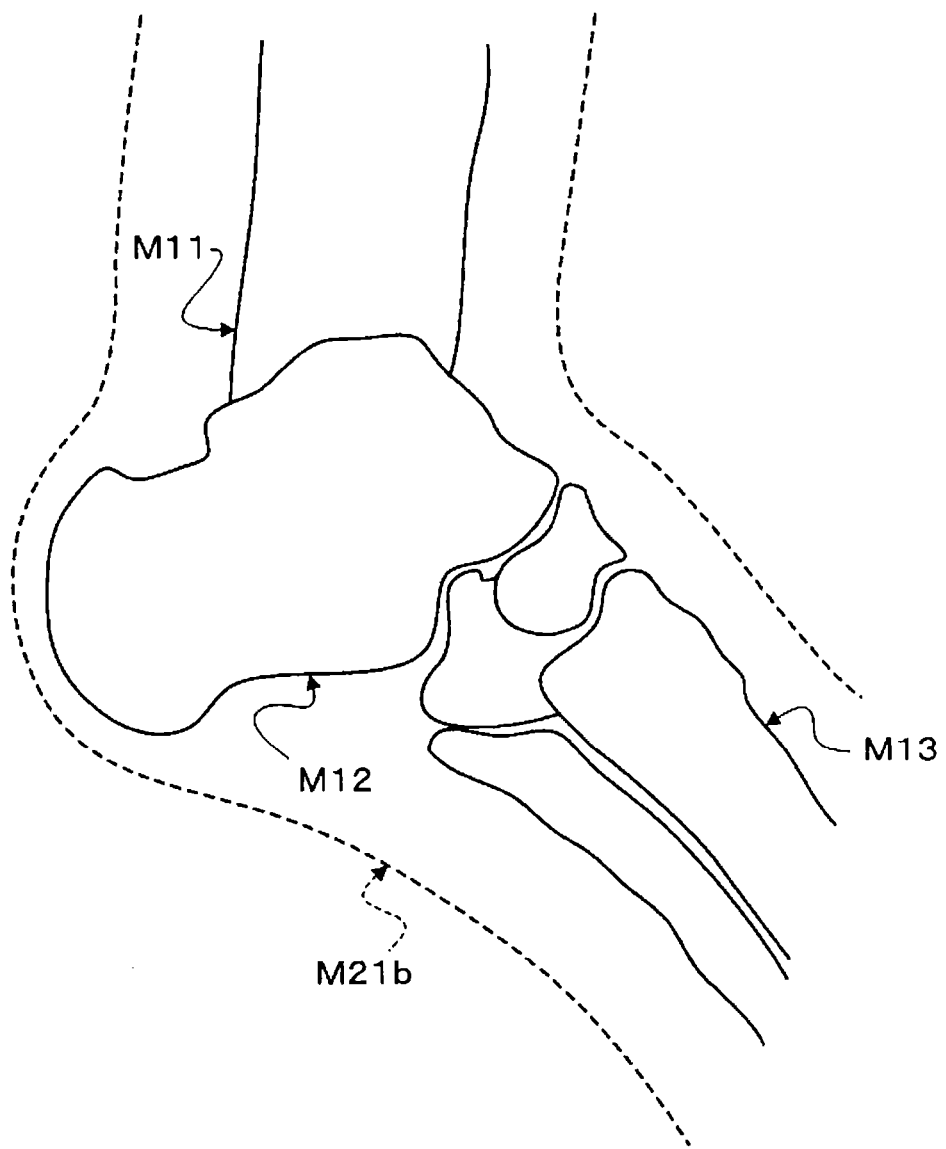
FIG. 4B explains the analysis of the shape based on the surface layer of the test object.

The object extracting part 211 sequentially receives the first image data for each timing point from the configuration extracting part 21. The object extracting part 211 according to the present embodiment detects the surface layer of the test object based on voxel data in this first image data, and extracts the object in the region formed by the detected surface layer. This object represents the outline shape of the test object. Hereinafter, sometimes this object is referred to as the outline object. Here, FIGS. 4A and 4B are referred. FIGS. 4A and 4B are the views for explaining analysis of the shape based on the surface layer of the test object. FIGS. 4A and 4B illustrate joint parts between an antebrachial region and a brachial region, with each of them corresponding to different timing points, respectively. The objects M11 to M13 in FIG. 4A represent the objects of the bones, while M21a denotes the outline object. In addition, the objects M11 to M13 in FIG. 4B represent the objects of the bones, and they correspond to the objects M11 to M13 in FIG. 4A. In addition, M21b in FIG. 4B denotes the outline object at a different timing point from that of FIG. 4A, and represents the different shape from the object M21a by the movement of the joint.

The object extracting part 211 outputs information indicating the outline object (for example, information indicating the shape, the position, and the size of the object) extracted for each of the first image data at each timing point (that is, extracted for each timing point) to the position analyzing unit 212 as related to the information indicating the corresponding timing point.

The position analyzing unit 212 receives the information indicating the outline object from the object extracting part 211 for each timing point. The position analyzing unit 212 analyzes changes in the outline along a time sequence based on this information. An example of a specific method thereof will be described below.

(In the Case of Changing the Frame Rate)

At first, the position analyzing unit 212 identifies a standard object from the outline objects for each timing point. As a specific example of a method of identifying this standard object, the position analyzing unit 212 analyzes each shape of the outline object for each timing point and identifies the object of a specific shape (satisfying the specific conditions). In the case of identifying the object of this specific shape, for example, the position analyzing unit 212 identifies a standard object by storing the information of the object with a standard shape in advance and comparing this with the outline object for each timing point, respectively. This comparison may be carried out via comparison of the outline shapes of the objects, or the standard object may be identified by extracting a plurality of shape features and comparing these features. In addition, the standard object may be identified by extracting axes of the parts corresponding to the brachial region and the antebrachial region and comparing these axes.

In addition, the operator may specify the standard outline object via an operation part 402. In this case, the configuration extracting part 21 outputs a series of first image data to the image processor 22 to generate medical images for each timing point, then causes the display 401 to display the medical images via the display controller 30. The operation part 402 receives the standard medical image selected from the displayed image data from the operator to notify the position analyzing unit 212 of the timing point corresponding to this medical image. Upon receiving this notification, the position analyzing unit 212 may identify the outline object corresponding to the notified timing point. Hereinafter, sometimes this standard outline object is referred to as a "standard object."

Identifying the standard object, the position analyzing unit 212 compares this standard object, the outline object for each timing point, and the standard object with each other, calculating the change amount between the objects for each timing point. Specifically, the position analyzing unit 212 compares the shapes of both objects, and calculates the difference (for example, the number of pixels of the part not overlapping between the objects) as the change amount. In addition, as another method, for example, extracting the axes from the brachial region and the antebrachial region, respectively, the position analyzing unit 212 may obtain the change amount based on the positional relationship between these axes (for example, the angle and the distance).

When the change amount is calculated for each timing point, the position analyzing unit 212 determines whether or not this change amount is within the predetermined amount (hereafter, referred to as a "specific amount"), then identifies the time width in which the change amount is formed by a timing point within the specific amount. This specific amount may be decided in advance, for example, based on a flexible range to be focused on in a series of movements of the observation object. This time width corresponds to a time width T21 (refer to FIG. 2E) in the first embodiment, and other time widths correspond to time widths T11 and T12. Hereinafter, the position analyzing unit 212 will be described assuming that this time width T21 is identified. The position analyzing unit 212 notifies the reconfiguration processing unit 14 of the identified time width T21.

(In the Case of Changing the Scanning Conditions and the Scan Stopping Process)

The position analyzing unit 212 analyzes the shape of each outline object for each timing point, and determines whether or not the shape corresponds to the specific shape (whether or not it satisfies the specific conditions). In the case of determining whether or not the shape corresponds to this specific shape, for example, the position analyzing unit 212 determines this specific shape by storing the information indicating the standard shape in advance, and comparing this with each outline object for each timing point. This comparison may be carried out due to comparison of the outline shape of the object, or may identify the specific shape by extracting a plurality of shape features and comparing these shape features. In addition, the specific shape may be identified by extracting the axes of the parts corresponding to the brachial region and the antebrachial region, and comparing these axes. Further, this specific shape may be decided in advance, for example, based on the shape of the observation object corresponding to a timing point desired to control the scan in a series of movements in the observation object (in other words, a shape corresponding to a timing point desired to change the scanning conditions, or desired to stop the scan).

In addition, obtaining images of the appearance of the observation object (hereinafter, referred to as an appearance image) in advance by a photographing unit for imaging an appearance (for example, a camera, etc.), the observation object, the position analyzing unit 212 may determine whether or not the shape of the outline object corresponds to this appearance image.

The determination of correspondence is not necessarily limited to complete correspondence and includes a case of high degree of correspondence as a result of matching by means of external images obtained by imaging the observation subject, for example. These external images may be projection data, perspective data through computed tomography or angiography, or data obtained by videography.

In this case, obtaining the information indicating the positional relationship between this photographing unit and the test object, the position analyzing unit 212 may identify the imaging position of this photographing unit based on this information. In this case, with this imaging position as a viewpoint, the position analyzing unit 212 may project the shape of the outline object and the outline object, and compare the projection with the appearance image.

Thus, the position analyzing unit 212 sequentially analyzes the information indicating the outline object to be sequentially output from the object extracting part 211 for each timing point, and determines whether or not the shape of the outline object corresponds to the specific shape. Thereby, the position analyzing unit 212 detects the timing point wherein the outline object has a specific shape. This timing point corresponds to "one timing point." Upon detecting this timing point, the position analyzing unit 212 instructs the scan control 501 to change the scanning conditions or stop the scan. Upon receiving these instructions, the scan control 501 carries out the instructed operation (that is, it changes the scanning conditions or stops the scan). Whether changes in the scanning conditions or stopping of the scan should be instructed may be related to the information indicating the detected timing point (in other words, the shape corresponding to this timing point) in advance.

(Commonalities in the Case of Changing the Frame Rate, Changing the Scanning Conditions, and the Scan Stopping Process)

Further, the following processing is the same as the first embodiment. In other words, the reconfiguration processing unit 14 carries out reconfiguration processing while changing the reconstruction conditions in the notified time width T21, and other time widths T11 and T12, then reconstructs image data for display for each timing point based on the reconstruction conditions. The reconfiguration processing unit 14 causes the image data storage 10 to store the reconstructed series of image data for display. As other embodiments, when the reconstructed second projected data for display is stored in the image data storage 10, the configuration extracting part 21 reads this data and transfers it to the image processor 22. Further, the first image data generated for analysis may be operated so as to be also used for display. In this case, the position analyzing unit 212 may transfer the image data that has already been read for analysis to the image processor 22. The image processor 22 carries out image processing on this image data and generates medical images, storing these medical images in the image storage 23 as related to the information indicating a corresponding timing point. The display controller 30 reads these medical images from the image storage 23 and arranges these medical images along a time sequence to cause the display 401 to display them as motion images.

Figure 3C:
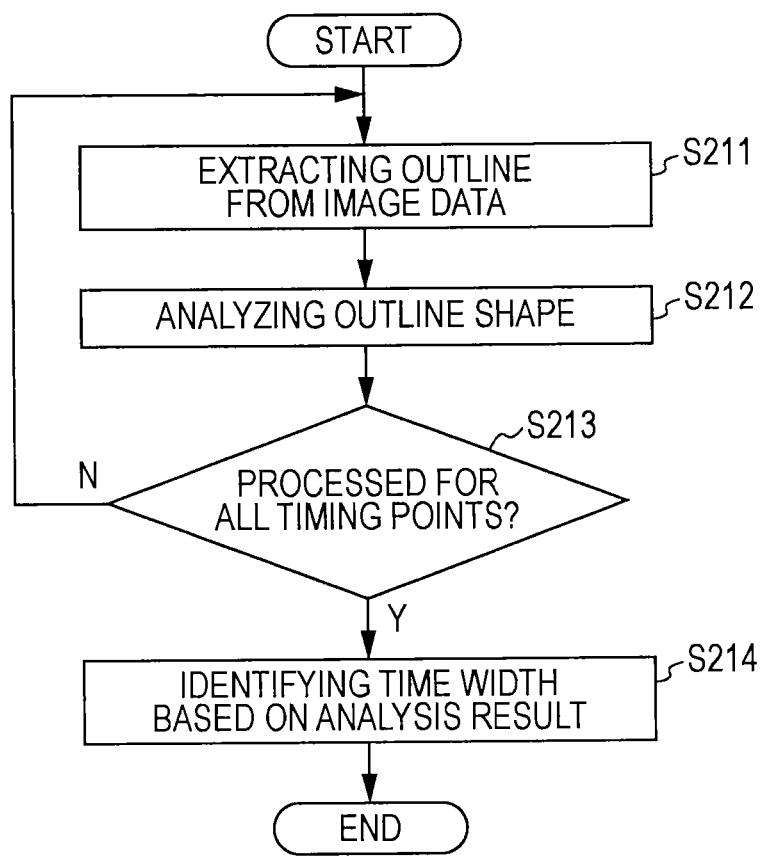
FIG. 3C is a flow chart showing the operations related to the analysis of the positional relation of Embodiment 2.

Next, with reference to FIGS. 3A and 3C, the series of operations of a medical image processing apparatus according to the present embodiment will be described. FIG. 3C is a flow chart showing the operation related to the analysis of the positional relationship according to the present embodiment. Further, the flow chart shown in FIG. 3C corresponds to the processing of Step S20 in FIG. 3A. In addition, processing other than the processing related to Step S11 and Step S20 in FIG. 3A and FIG. 5 is the same as that of the first embodiment. Therefore, an explanation will be provided focusing on the processes related to Step S11 and Step S20 different from the first embodiment, namely, the processes related to Steps S211 to S214 illustrated in FIG. 3C.

(Step S11)

The reconfiguration processing unit 14 sequentially reads the acquired projected data from the projected data storage 13 in parallel with the processing for acquiring projected data by means of the X-ray photographing unit 500. The reconfiguration processing unit 14 generates image data for each timing point based on these reconstruction conditions by carrying out reconfiguration processing on this read projected data based on the predetermined reconstruction conditions for analysis. Further, according to the present embodiment, these reconstruction conditions are configured so as to be capable of extracting the surface layer of the test object from the projected data (that is, skin). Specifically, these reconstruction conditions have a range of CT numbers that is a target of reconstruction, which is adjusted at a level capable of extracting the surface layer. Thereby, this image data is reconstructed so as to be capable of extracting the surface layer. The reconfiguration processing unit 14 causes the image data storage 10 to store the image data generated for each timing point.

According to the present embodiment, the reconstruction conditions for reconstructing the image data for analysis are configured so as to be capable of extracting the surface layer of the test object from the projected data (that is, skin). Specifically, these reconstruction conditions have a range of CT numbers that is a target of reconstruction, which is adjusted at a level capable of extracting the surface layer. Thereby, this image data is reconstructed so as to be capable of extracting the surface layer. The reconstruction conditions in this case correspond to "first conditions" in the present embodiment, and the image data generated based on these reconstruction conditions corresponds to "first image data." The reconfiguration processing unit 14 causes the image data storage 10 to store the image data generated for each timing point.
(Step S211)

At first, the configuration extracting part 21 reads the first image data reconstructed for analysis for each timing point. The configuration extracting part 21 sequentially reads the image data for analysis sequentially generated by the reconfiguration processing unit 14 for each timing point and stored in the image data storage 10 from the image data storage 10. In this case, the operation by the reconfiguration processing unit 14 and the operation for reading the image data for analysis by the configuration extracting part 21 may be synchronized with each other. The configuration extracting part 21 outputs each of the read first image data for each timing point to the object extracting part 211, and instructs it to extract the object. This operation of the configuration extracting part 21 is identical with the first embodiment.

The object extracting part 211 sequentially receives the first image data for each timing point from the configuration extracting part 21. The object extracting part 211 according to the present embodiment detects the surface layer of the test object based on voxel data in this first image data, and extracts the object in the region formed by the detected surface layer. This object represents the outline shape of the test object. Hereinafter, this object is sometimes referred to as the outline object. The object extracting part 211 outputs information indicating the outline object (for example, objects M21a and M21b in FIG. 4A and FIG. 4B) extracted for each of the first image data at each timing point (that is, extracted for each timing point) to the position analyzing unit 212 as related to the information indicating the corresponding timing point.

Here, FIG. 4A and FIG. 4B are referred. FIG. 4A and FIG. 4B are the views for explaining analysis of the shape based on the surface layer of the test object. FIGS. 4A and 4B illustrate joint parts between the antebrachial region and the brachial region, with each of them corresponding to different timing points, respectively. The objects M11 to M13 in FIG. 4A represent the objects of the bones, while M21a denotes the outline object. In addition, the objects M11 to M13 in FIG. 4B represent the objects of the bones and correspond to the objects M11 to M13 in FIG. 4A. In addition, M21b in FIG. 4B denotes the outline object at a different timing point from that of FIG. 4A, representing a different shape from the object M21a by the movement of the joint.

The object extracting part 211 outputs information indicating the outline object (for example, information indicating the shape, the position, and the size of the object) extracted for each of the first image data at each timing point (that is, extracted for each timing point) to the position analyzing unit 212 as related to the information indicating the corresponding timing point.
(Step S212)

The position analyzing unit 212 receives the information indicating the outline object from the object extracting part 211 for each timing point. The position analyzing unit 212 analyzes changes in the outline along a time sequence based on this information. Specifically, at first, the position analyzing unit 212 identifies a standard object from the outline objects for each timing point. As a specific example of a method of identifying this standard object, the position analyzing unit 212 analyzes each shape of the outline object for each timing point and identifies the object of a specific shape (satisfying the specific conditions).
(In the Case of Changing the Scanning Conditions and the Scan Stopping Process)

The position analyzing unit 212 analyzes the shape of each outline object for each timing point, and determines whether or not the shape corresponds to the specific shape (whether or not it satisfies the specific conditions). In the case of determining whether or not the shape corresponds to this specific shape, for example, the position analyzing unit 212 determines this specific shape by storing the information indicating the standard shape in advance, and comparing this with each outline object for each timing point. This comparison may be carried out due to comparison of the outline shape of the object, or may identify the specific shape by extracting a plurality of shape features and comparing these shape features. In addition, the specific shape may be identified by extracting the axes of the parts corresponding to the brachial region and the antebrachial region, and comparing these axes. Further, this specific shape may be decided in advance, for example, based on the shape of the observation object corresponding to a timing point desired to control the scan in a series of movements in the observation object (in other words, a shape corresponding to a timing point desired to change the scanning conditions, or desired to stop the scan).

Thus, the position analyzing unit 212 sequentially analyzes the information indicating the outline object to be sequentially output from the object extracting part 211 for each timing point, and determines whether or not the shape of the outline object corresponds to the specific shape. Thereby, the position analyzing unit 212 detects the timing point wherein the outline object has a specific shape. This timing point corresponds to "one timing point."

Further, the following processing is the same as the first embodiment. In other words, upon detecting a timing point, the position analyzing unit 212 instructs the scan control 501 to change the scanning conditions or stop the scan. Upon receiving these instructions, the scan control 501 carries out the instructed operation (that is, it changes the scanning conditions or stops the scan).

As described above, the X-ray CT system according to the present embodiment analyzes changes in the positional relationship between at least two or more sites configuring flexible sites due to changes in the shape of the outline of the test object, the flexible sites being related to a surgery site of muscules, tendons or bones such as a joint and a spondylus. Moreover, the X-ray CT system detects a timing point in which the shape of the outline corresponds to a specific shape, and based on this timing point, it controls the operation related to acquisition of the projected data (that is, it changes the scanning conditions or stops the scan). Thereby, in the X-ray CT system according to the present embodiment, the X-ray CT system itself can automatically control the operation for acquiring projected data without the operator when a positional relationship between two or more sites satisfies specific conditions.
(In the Case of Changing the Frame Rate)

Identifying the standard object, the position analyzing unit 212 compares this standard object, the outline object for each timing point, and the standard object with each other, calculating the change amount between the objects for each timing point. Specifically, the position analyzing unit 212 compares the shapes of both objects and calculates the difference (for example, the number of pixels of the part not overlapping between the objects) as the change amount.
(Step S213)
When a timing point in which the change amount is not calculated exists (Step S213,N), the position analyzing unit 212 calculates the change amount by comparing the outline object corresponding to this timing point with the standard object.
(Step S214)
Calculating the change amount for each timing point (Step S213,Y), the position analyzing unit 212 determines whether or not this change amount is within the range of predetermined amount (hereinafter, referred to as the "specific amount"), and identifies the time width that is formed by a timing point having the change amount within the specific amount. This time width corresponds to the time width T21 (refer to FIG. 2E) in the first embodiment, while other time widths correspond to the time widths T11 and T12. Hereinafter, the position analyzing unit 212 will be described assuming that this time width T21 is identified. The position analyzing unit 212 notifies the reconfiguration processing unit 14 of the identified time width T21.

Further, the following processing is the same as the first embodiment. In other words, the reconfiguration processing unit 14 carries out reconfiguration processing while changing the reconstruction conditions in the notified time width T21, and other time widths T11 and T12, then reconstructs image data for display for each timing point based on the reconstruction conditions. The reconfiguration processing unit 14 causes the image data storage 10 to store the reconstructed series of image data for display. The image processor 22 carries out image processing on this image data and generates medical images, storing these medical images in the image storage 23 as related to the information indicating a corresponding timing point. The display controller 30 reads these medical images from the image storage 23 and arranges these medical images along a time sequence to cause the display 401 to display them as motion images.

As described above, the medical image processing apparatus according to the present embodiment analyzes changes in the positional relationship between at least two or more sites temporarily working with each other in accordance with changes in the shape of the outline of the test object, the flexible sites being related to a surgery site of muscles, tendons or bones such as a joint and a spondylus. Moreover, the medical image processing apparatus identifies a time width in which the change amount of the shape is included in the specific range. Thereby, with respect to a time width in which the positional relationship in two or more sites is included in the specific range, the medical image processing apparatus according to the present embodiment can display the medical images at a higher frame rate than other time widths similar to the first embodiment.

Third Embodiment

Next, the medical image processing apparatus according to the third embodiment will be described. In the first and the second embodiments, for example, based on the case in which the joint of the test object has a predetermined shape, identifying the time width to change the reconstruction conditions, the operation related to acquisition of the projected data is controlled. The medical image processing apparatus according to the present embodiment identifies the time width to change the reconstruction conditions in accordance with the change amount per unit time, and the control timing point related to acquisition of the projected data. Specifically explaining this with an example, as the speed of the movement of the observation object such as a joint is not always constant, in the case of displaying a series of operations at the same frame rate, sometimes it is difficult to observe fine movements of the observation object at a timing point in which the observation object moves fast. Therefore, the medical image processing apparatus according to the present embodiment reconstructs a time width in which the observation object (for example, each site configuring the joint) is moving fast at a higher volume rate than other time widths. Alternatively, detecting that the observation object is moving fast, based on this timing point, the scanning conditions are changed such that, at a high resolving power, the projected data is acquired. Due to such a configuration, when the observation object moves fast, by increasing the frame rate, it becomes possible to display the observation object such that fine movements thereof can be observed. Hereinafter, the configuration of the medical image processing apparatus according to the present embodiment will be described focusing on parts different from the first embodiment.

(In the Case of Changing the Frame Rate)
At first, the reconfiguration processing unit 14 carries out reconfiguration processing on the read projected data based on the predetermined reconstruction conditions for analysis, then generates image data for each timing point based on these reconstruction conditions. Here, it is described assuming that these reconstruction conditions are configured so as to be capable of extracting the bones in the test object from the projected data, similar to the first embodiment. The reconfiguration processing unit 14 causes the image data storage 10 to store image data generated for each timing point.

Further, processing for reconstructing image data for display by the reconfiguration processing unit 14 according to the present embodiment is identical with the operation of the reconfiguration processing unit 14 according to the first embodiment. In other words, the reconfiguration processing unit 14 receives notification of a time width T21 including a plurality of timing points from the position analyzing unit 212. The reconfiguration processing unit 14 carries out reconfiguration processing while changing the reconstruction conditions in the notified time width T21, and other time widths T11 and T12, then reconstructs image data for display to cause the image data storage 10 to store the reconstructed image data.

At first, the configuration extracting part 21 reads the first image data reconstructed for analysis for each timing point. The configuration extracting part 21 outputs each of the read first image data for each timing point to the object extracting part 211, and instructs it to extract the object. Upon receiving these instructions, the object extracting part 211 extracts the objects of the bones based on voxel data in this first image data. The object extracting part 211 outputs information indicating the objects of the bones extracted for each of the first image data at each timing point to the position analyzing unit 212 as related to the information indicating the corresponding timing point. The operations of this configuration extracting part 21 and object extracting part 211 are identical with the first embodiment.

The position analyzing unit 212 receives the information indicating the objects of the bones from the object extracting part 211 for each timing point. The position analyzing unit 212 identifies the positional relationship of the bones at each timing point based on this information. This identifying method is the same as the first embodiment. Hereinafter, it is described assuming that, as illustrated in FIGS. 2A to 2C, the planes P11 and P13 are extracted from the objects M11 and M13, and based on this, the positional relationship between the objects M11 and M13 is identified.

When the positional relationship between the objects M11 and M13 is identified with respect to a series of timing points, the position analyzing unit 212 compares the positional relationships formed by the objects M11 and M13 between the adjacent timing points in order to calculate the change amount. This comparison of the positional relationship may be calculated based on the angle and/or the distance of the planes P11 and P13 similar to the first embodiment. The first image data is reconstructed at a constant volume rate across the entire series of time widths. Therefore, if the change amount between the adjacent timing points is calculated, this change amount is increased particularly between the timing points in which the test object is moving fast. In other words, the position analyzing unit 212 determines whether or not each change amount calculated between the adjacent timing points is not less than a predetermined amount (hereinafter, referred to as the "specific amount") and identifies a time width formed between the timing points with a change amount no less than the specific amount. This time width corresponds to the time width T21 (refer to FIG. 2E) in the first embodiment, while other time widths correspond to the time widths T11 and T12. Hereinafter, it is explained that the position analyzing unit 212 identifies this time width T21. The position analyzing unit 212 notifies the reconfiguration processing unit 14 of the identified time width T21.

The following processes are identical with the first embodiment. In other words, the reconfiguration processing unit 14 carries out reconfiguration processing while changing the reconstruction conditions between the notified time width T21 and other time widths T11 and T12, then reconstructs the image data for display for each timing point based on the reconstruction conditions. The reconfiguration processing unit 14 causes the image data storage 10 to store the reconstructed series of image data for display. The image processor 22 carries out image processing on this image data and generates medical images, storing these medical images in the image storage 23 as related to the information indicating a corresponding timing point. The display controller 30 reads these medical images from the image storage 23 and arranges these medical images along a time sequence to cause the display 401 to display them as motion images.

Further, in the above description, similar to the first embodiment, the time width T21 to change the reconstruction conditions is identified based on the positional relationship between the objects of the bones; however, similar to the second embodiment, the time width T21 may be identified based on the change in the shape of the outline of the test object. In this case, the position analyzing unit 212 may compare the outline objects between the adjacent timing points and may define the difference as the change amount.

As described above, the medical image processing apparatus according to the present embodiment identifies the time width to change the reconstruction conditions in accordance with the change amount per unit time of at least two or more sites temporally working with each other, the flexible sites being related to a surgery site of muscles, tendons or bones such as a joint and a spondylus. Moreover, with respect to the identified time width, the image data is reconstructed at a higher volume rate than other time widths. Thereby, the medical image processing apparatus according to the present embodiment can display the medical images at a high frame rate when the observation object is moving fast.
(In the Case of Changing the Scanning Conditions and the Scan Stopping Process)

The X-ray CT system according to the present embodiment grasps the position and direction of respective sites configuring the observation object as well as the relative positional relationship thereof (hereinafter, it is simply referred to as the "positional relationship") by analyzing the reconstructed image data. Therefore, the reconfiguration processing unit 14 reconstructs image data for analysis separately from the image data for display. Specifically, the reconfiguration processing unit 14 sequentially reads the acquired projected data from the projected data storage 13 in parallel with processing for acquiring projected data by means of the X-ray photographing unit 500. The reconfiguration processing unit 14 generates image data for analysis for each timing point based on these reconstruction conditions by carrying out reconfiguration processing on this read projected data based on the predetermined reconstruction conditions for analysis.

According to the present embodiment, the reconstruction conditions for reconstructing the image data for analysis is configured so as to be capable of extracting the bones in the test object from the projected data. In other words, this image data is reconstructed so as to be capable of extracting the bones. Further, sometimes the reconstruction conditions in this case are referred to as "first conditions" and the image data generated based on these reconstruction conditions is referred to as "first image data." The reconfiguration processing unit 14 causes the image data storage 10 to store the image data sequentially generated for each timing point.

Further, processing for reconstructing image data for display by the reconfiguration processing unit 14 according to the present embodiment is identical with the operation of the reconfiguration processing unit 14 according to the first embodiment. In other words, the reconfiguration processing unit 14 generates image data for display for each timing point based on these reconstruction conditions by reading the projected data from the projected data storage 13 and carrying out reconfiguration processing based on the predetermined reconstruction conditions for display. Hereinafter, sometimes the reconstruction conditions for display are referred to as "second conditions" and the image data generated based on these reconstruction conditions are referred to as "second projected data." The reconfiguration processing unit 14 causes the image data storage 10 to store this image data for display generated for each timing point.

The image data for display is not always needed to be operated in parallel with the processing for obtaining projected data. For example, the reconfiguration processing unit 14 may reconstruct the image data for display after a series of projected data is obtained. This operation is also identical with the first embodiment.

The configuration extracting part 21 sequentially reads from the image data storage 10 the image data for analysis sequentially generated by the reconfiguration processing unit 14 for each timing point and stored in the image data storage 10. In this case, the operation by the reconfiguration processing unit 14 and the operation for reading the image data for analysis by the configuration extracting part 21 may be synchronized with each other. The configuration extracting part 21 successively outputs the first image per read-out timing to the object extracting part 211, and instructs extraction of the object from the first image data. This operation of the configuration extracting part 21 is the same as the first embodiment.

The object extracting part 211 sequentially receives the first image data for each timing point from the configuration extracting part 21. The object extracting part 211 extracts the objects of the bones based on voxel data in this first image data. The object extracting part 211 sequentially outputs information indicating the objects of the bones extracted for each of the first image data at each timing point to the position analyzing unit 212 as related to the information indicating the corresponding timing point. These operations of the configuration extracting part 21 and the object extracting part 211 are the same as the first embodiment.

The position analyzing unit 212 sequentially receives the information indicating the objects of the bones from the extracting part 211 for each timing point. The position analyzing unit 212 identifies the positional relationship of the bones at each timing point based on this information. This identifying method is the same as the first embodiment. Hereinafter, it is described assuming that, as illustrated in FIGS. 2A to 2C, the planes P11 and P13 are extracted from the objects M11 and M13, and based on this, the positional relationship between the objects M11 and M13 is identified.

When the positional relationship formed by the objects M11 and M13 is identified, the position analyzing unit 212 compares the positional relationships formed by the objects M11 and M13 between the adjacent timing points to calculate the change amount. This comparison of the positional relationship may be calculated based on the angle and the distance of the planes P11 and P13 similar to the first embodiment. If the change amount between the adjacent timing points is calculated, this change amount is increased particularly between the timing points in which the test object is moving fast. In other words, the position analyzing unit 212 determines whether or not the change amount calculated between the adjacent timing points is not less than a predetermined amount (hereinafter, referred to as a "specific amount") and identifies a time width formed between the timing points with a change amount no less than the specific amount.

Thus, the position analyzing unit 212 sequentially calculates the change amount between the adjacent timing points, then determines whether or not the calculated change amount is not less than the specific amount. Thereby, the position analyzing unit 212 detects a timing point in which the change amount between the adjacent timing points is no less than the specific amount, namely, a timing point in which the speed of the operating test object is made faster. Further, this timing point corresponds to "one timing point." Detecting this timing point, the position analyzing unit 212 instructs the scan control 501 to change the scanning condition or stop the scan. Upon receiving these instructions, the scan control 501 carries out the instructed operation (that is, change of the scanning condition or stop the scan). Whether change of the scanning condition or stop of the scan should be instructed may be related to the information indicating the detected timing point (in other words, the change amount for detecting the timing point) in advance.

In addition, the position analyzing unit 212 may be operated so as to determine whether or not the change amount is not more than the specific amount. For example, the position analyzing unit 212 may detect a timing point in which the change amount is no more than the specific amount, and based on this timing point, may instruct the scan control 501 to stop the scan. By causing the position analyzing unit 212 to thus operate, for example, at a timing point in which the joints completely bend and the positional relationship between the sites constructing the joints never changes, it becomes possible to cause the X-ray CT system itself to stop acquisition of the projected data.

Further, the following operations are the same as the first embodiment. In other words, if the second projected data reconstructed for display is stored in the image data storage 10, the configuration extracting part 21 reads this and transfers it to the image processor 22. The first image data generated for analysis may be operated for display. In this case, the position analyzing unit 212 may transfer the image data that has been already read for analysis to the image processor 22. The image processor 22 carries out the image processing on this image data and generates medical images, storing these medical images in the image storage 23 as related to the information indicating a corresponding timing point. The display controller 30 reads these medical images from the image storage 23 and arranges these medical images along a time sequence to cause the display 401 to display them as motion images.

Further, in the above description, similar to the first embodiment, based on the positional relationship between the objects of the bones, the timing point in which the operation related to acquisition of the projected data is controlled is identified; however, similar to the second embodiment, based on the change in the shape of the outline of the test object, this timing point may be identified. In this case, the position analyzing unit 212 may compare the outline object between the adjacent timing points and may define the difference as the change amount.

As described above, the X-ray CT system according to the present embodiment controls the operation related to acquisition of the projected data in accordance with the change amount per unit time of the positional relationship between at least two or more sites constructing a flexible site related to a surgery site of muscles, tendons or bones such as a joint and a spondylus. Thereby, in the X-ray CT system according to the present embodiment, the X-ray CT system itself can automatically control the operation related to acquisition of the projected data without the operator when the positional relationship between two or more sites satisfies the specific conditions.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
   a photographing unit configured to scan a flexible site of the living body having a plurality of components in order to obtain projected data,
   a reconfiguration processing unit configured to carry out reconfiguration processing on the projected data to generate image data of the flexible site at a plurality of timing points,
   an extracting unit configured to extract the plurality of components configuring the flexible site from the respective image data, and
   an analyzing unit configured to determine a positional relation of the plurality of extracted components configuring the flexible site at the plurality of timing points and to specify image data of a specific timing point through conditional determination of the obtained positional relation, the specific timing point corresponding to the determination result.

2. The medical image processing apparatus according to claim 1, wherein the reconfiguration processing unit is configured to carry out reconstructing processing on the projected data at a first frame rate to generate first image data of the flexible site, the extracting unit is configured to extract the plurality of components from the first image data, and the reconfiguration processing unit is further configured to carry out reconfiguration processing at a second frame rate, which is different from the first frame rate, on the projected data within the specific timing from among the projected data regarding the specific timing point specified by the analyzing unit, to generate second image data.

3. The medical image processing apparatus according to claim 2, wherein the sites are bones, the extracting unit is configured to respectively extract the bones, and the analyzing unit is configured to carry out the conditional determination of the positional relation of the bones configuring the extracted flexible site.

4. The medical image processing apparatus according to claim 2, wherein the analyzing unit is configured to form planes from three or more points of shape characteristics regarding the respective extracted components and to determine the positional relation of two of the formed planes, to realize the positional relation of the components.

5. The medical image processing apparatus according to claim 4, wherein the analyzing unit is configured to carry out the conditional determination of the positional relation of the planes based on the angle configured from the two formed planes.

6. The medical image processing apparatus according to claim 4, wherein the analyzing unit is configured to carry out the conditional determination of the positional relation of the planes based on a distance between the two formed planes.

7. The medical image processing apparatus according to claim 2, wherein the analyzing unit is configured to connect two points of shape characteristics regarding the respective extracted components in order to shape lines, and to determine the positional relation of the two shaped lines, to realize the positional relation of the components.

8. The medical image processing apparatus according to claim 2, wherein the analyzing unit is configured to specify the positional relation of the components based on outlines of the extracted components.

9. The medical image processing apparatus according to claim 2, wherein the analyzing unit is configured to specify the positional relation of the components based on information showing shades of the extracted components.

10. The medical image processing apparatus according to claim 2, wherein the extracting unit is configured to extract the plurality of components based on surface layers of the plurality of components.

11. The medical image processing apparatus according to claim 2, wherein the extracting unit extracts a region containing the respective sites configuring the flexible site based on the respective surface layers of a tissue, and the analyzing unit conditionally determines the amount of change between the shape of the region and a shape determined in advance.

12. The medical image processing apparatus according to claim 2, wherein the analyzing unit calculates the amount of change in the position of the plurality of components between the pluralities of timing points, and conditionally makes a determination based on the calculated amount of change.

13. The medical image processing apparatus according to claim 2, comprising one timing point specifying unit that specifies one timing point in the projected data in advance, wherein, with the positional relation of the plurality of components corresponding to the specific timing point as the standard, the analyzing unit conditionally makes a determination based on the amount of change from the standard.

14. The medical image processing apparatus according to claim 1, further comprising a controlling means for stopping the acquisition of the projected data or changing the imaging conditions by means of the photographing unit when the specific timing point is specified according to the conditional determination by the analyzing unit.

15. The medical image processing apparatus according to claim 14, wherein the sites are bones, the extracting unit respectively extracts the bones, and the analyzing unit conditionally determines the positional relation of the bones configuring the extracted flexible site.

16. The medical image processing apparatus according to claim 14, wherein the analyzing unit shapes surfaces shaped from three or more points of shape characteristics regarding the respective plurality of extracted components and conditionally determines the positional relation of the surface corresponding with the components, thereby specifying the specific timing point.

17. The medical image processing apparatus according to claim 16, wherein the analyzing unit calculates the angle configured from the surfaces corresponding with the plurality of shaped components, specifies the image data wherein the calculated angle is the predetermined angle, and realizes the timing point corresponding to the image data as the specific timing point.

18. The medical image processing apparatus according to claim 16, wherein the analyzing unit calculates the distance between the surfaces corresponding with the plurality of shaped components, specifies the image data in which the calculated distance is the predetermined distance, and realizes the timing corresponding to the image data as the specific timing point.

19. The medical image processing apparatus according to claim 14, wherein the analyzing unit shapes the lines shaped by two points of shape characteristics regarding the respective plurality of extracted components, and conditionally determines the positional relation of the line corresponding to the components.

20. The medical image processing apparatus according to claim 14, wherein the analyzing unit specifies the positional relation of the components based on the external form of the respective plurality of extracted components.

21. The medical image processing apparatus according to claim 14, wherein the analyzing unit specifies the positional relation of the components based on information showing the shades of the respective plurality of extracted components.

22. The medical image processing apparatus according to claim 14, wherein the extracting unit extracts the plurality of components based on the respective surface layers of the flexible site.

23. The medical image processing apparatus according to claim 14, wherein the extracting unit extracts the plurality of components as the region comprising a plurality of components based on the surface layers of the flexible site, and the analyzing unit specifies the timing point in which the shape of the region between the pluralities of timing points corresponds with the shape determined in advance, and realizes the timing point corresponding to the image data as the specific timing point.

24. The medical image processing apparatus according to claim 1, wherein the analyzing unit successively analyzes the positional relation of the plurality of components extracted from the image data for each of the timing points between adjacent timing points and conditionally determines the amount of change of the positional relation between the timing points, thereby specifying the specific timing point corresponding with the determination result.

25. The medical image processing apparatus according to claim 1, wherein the analyzing unit successively analyzes the positional relation of the plurality of components extracted from the image data for each of the timing points, specifies the specific timing point in which the plurality of components achieves the predetermined positional relation, and supplements information to distinguish from other image data with respect to the image data corresponding to the specific timing point.

* * * * *